(12) United States Patent
Schmidt et al.

(10) Patent No.: US 10,253,792 B2
(45) Date of Patent: Apr. 9, 2019

(54) FLUID WASTE COLLECTION AND DISPOSAL SYSTEM AND METHOD

(71) Applicant: Skyline Medical Inc., Eagan, MN (US)

(72) Inventors: Rodney Schmidt, Maplewood, MN (US); David Johnson, Bloomington, MN (US); David Dauwalter, Chaska, MN (US)

(73) Assignee: Skyline Medical, Inc., Eagan, MN (US)

( * ) Notice: Subject to any disclaimer, the term of this patent is extended or adjusted under 35 U.S.C. 154(b) by 82 days.

(21) Appl. No.: 14/763,459

(22) PCT Filed: Jan. 25, 2014

(86) PCT No.: PCT/US2014/013081
§ 371 (c)(1),
(2) Date: Jul. 24, 2015

(87) PCT Pub. No.: WO2014/117043
PCT Pub. Date: Jul. 31, 2014

(65) Prior Publication Data
US 2015/0362000 A1 Dec. 17, 2015

Related U.S. Application Data

(60) Provisional application No. 61/756,763, filed on Jan. 25, 2013.

(51) Int. Cl.
*F15D 1/00* (2006.01)
*B08B 3/04* (2006.01)
*A61M 1/00* (2006.01)

(52) U.S. Cl.
CPC ........... *F15D 1/002* (2013.01); *A61M 1/0007* (2014.02); *B08B 3/04* (2013.01); *A61M 1/0096* (2014.02); *Y10T 137/0396* (2015.04)

(58) Field of Classification Search
CPC ........ F15D 1/002; B08B 3/04; A61M 1/0007; A61M 1/0096; Y10T 137/0396
(Continued)

(56) References Cited

U.S. PATENT DOCUMENTS

| 4,384,580 A | 5/1983 | Leviton |
| 4,388,922 A | 6/1983 | Telang |

(Continued)

FOREIGN PATENT DOCUMENTS

| EP | 2065020 A1 | 6/2009 |

*Primary Examiner* — Kevin F Murphy
*Assistant Examiner* — Patrick C Williams
(74) *Attorney, Agent, or Firm* — Thomas J. Oppold; Larkin Hoffman Daly & Lindgren, Ltd.

(57) ABSTRACT

A system and method of collecting and disposing of fluid during a medical procedure. Fluid is drawn from a fluid source into a first reservoir in communication with a vacuum source. The fluid passes through an open fluid transfer valve into a second reservoir in communication with the vacuum source. While the fluid continues to be drawn into the first reservoir, the fluid transfer valve is closed after a predetermined volume of the fluid passes into the second reservoir. The fluid collected in the second reservoir is measured and evacuated from the second reservoir. The fluid transfer valve is opened and the steps are repeated until the medical procedure is completed while the first reservoir remains in uninterrupted communication with the vacuum source during the medical procedure such that fluid is capable of continuing to be drawn into the first reservoir without interruption.

20 Claims, 30 Drawing Sheets

(58) Field of Classification Search
USPC .......... 604/541, 543, 318–320; 137/396, 403
See application file for complete search history.

(56) References Cited

U.S. PATENT DOCUMENTS

| | | | |
|---|---|---|---|
| 4,534,765 A | 8/1985 | Todd et al. | |
| 4,569,674 A | 2/1986 | Phillips et al. | |
| 4,619,647 A | 10/1986 | Kurtz et al. | |
| 4,655,754 A | 4/1987 | Richmond et al. | |
| 4,693,271 A * | 9/1987 | Hargrove | E03B 11/10 137/565.17 |
| 4,795,448 A | 1/1989 | Stacey et al. | |
| 4,826,494 A | 5/1989 | Richmond et al. | |
| 4,863,446 A | 9/1989 | Parker | |
| 5,031,642 A | 6/1991 | Nosek | |
| 5,091,863 A | 2/1992 | Hungerford et al. | |
| 5,133,374 A | 7/1992 | Druding et al. | |
| 5,242,434 A | 9/1993 | Terry | |
| 5,286,262 A | 2/1994 | Herweck et al. | |
| 5,547,582 A | 8/1996 | Waibel | |
| 5,656,027 A | 8/1997 | Ellingboe | |
| 5,741,238 A | 4/1998 | Bradbury et al. | |
| 5,776,118 A | 7/1998 | Seifert et al. | |
| 5,807,359 A | 9/1998 | Bemis et al. | |
| 5,901,717 A | 5/1999 | Dunn et al. | |
| 5,914,047 A | 6/1999 | Griffiths | |
| 5,931,822 A | 8/1999 | Bemis et al. | |
| 5,945,004 A | 8/1999 | Ohira et al. | |
| 5,975,096 A | 11/1999 | Dunn et al. | |
| 5,989,234 A | 11/1999 | Valerio et al. | |
| 5,997,733 A | 12/1999 | Wilbur et al. | |
| 6,039,724 A | 3/2000 | Seifert et al. | |
| 6,152,902 A | 11/2000 | Christian et al. | |
| 6,180,000 B1 | 1/2001 | Wilbur et al. | |
| 6,263,887 B1 | 7/2001 | Dunn | |
| 6,368,310 B1 | 4/2002 | Bemis et al. | |
| 6,499,495 B2 | 12/2002 | Jeng | |
| 6,588,436 B2 | 7/2003 | Dunn et al. | |
| 6,652,495 B1 | 11/2003 | Walker | |
| 6,770,061 B2 | 8/2004 | Wildman | |
| 6,776,175 B2 | 8/2004 | Dunn et al. | |
| 6,796,317 B2 | 9/2004 | Dunn et al. | |
| 6,893,425 B2 | 5/2005 | Dunn et al. | |
| 7,090,663 B2 | 8/2006 | Dunn et al. | |
| 7,204,821 B1 | 4/2007 | Clare et al. | |
| 7,258,711 B2 | 8/2007 | Dunn et al. | |
| 7,267,666 B1 | 9/2007 | Duchon et al. | |
| 7,357,142 B2 | 4/2008 | Merkle | |
| 7,469,727 B2 | 12/2008 | Marshall | |
| 7,621,898 B2 | 11/2009 | Lalomia et al. | |
| 7,879,228 B2 | 2/2011 | Dunn et al. | |
| 7,892,420 B2 | 2/2011 | Dunn et al. | |
| 8,123,731 B2 | 2/2012 | Ryan | |
| 8,172,817 B2 | 5/2012 | Michaels et al. | |
| 8,226,549 B2 | 7/2012 | Kumar et al. | |
| 8,292,857 B2 | 10/2012 | Martini et al. | |
| 8,475,419 B2 * | 7/2013 | Eckermann | A61M 1/0031 604/187 |
| 2005/0187529 A1 | 8/2005 | Reasoner et al. | |
| 2005/0209585 A1 * | 9/2005 | Nord | A61L 11/00 604/540 |
| 2007/0135779 A1 | 6/2007 | Lalomia et al. | |
| 2009/0216205 A1 | 8/2009 | Ryan et al. | |
| 2010/0036335 A1 | 2/2010 | Murray et al. | |

* cited by examiner

Fluid In

Relief & Measure

Drain

Second Reservoir Preparation

Fluid In

Relief and Measure

Drain

Second Reservoir Preparation

Cleaning Solution In

Cleaning Solution Recirculation

Relief

Repeat Recirculation

Drain Cleaning Solution

Cleaning Solution Into
Second Reservoir

Cleaning Solution Into First Reservoir

Relief

Cleaning Solution Recirculation

First Reservoir Drain

Drain Cleaning Solution

FLUID WASTE COLLECTION AND DISPOSAL SYSTEM AND METHOD

BACKGROUND

Systems for collecting and disposing of bodily fluids and other fluids that are aspirated from a patient during surgical procedures are well known. Conventional fluid waste collection systems typically use some type of container or canister into which the aspirated fluids are collected. As the fluid collection canisters become filled during the course of a surgical procedure, the filled canisters are replaced with empty canisters. Depending on the volume of the canisters and the amount of fluid being collected, the surgical procedure may have to be interrupted to replace a filled canister with an empty canister.

It should be appreciated that the aspirated fluids may be contaminated with pathogens, such as HIV, HPV, Hepatitis, MRSA and other infectious agents. During the surgical procedure and/or after the surgical procedure is completed, the fluid filled canisters are typically carted from the operating room to a central collection location for disposal or, alternatively, the canisters may be emptied, cleaned, and re-used. Accordingly, handling of fluid collection canisters by hospital personnel creates a risk that the handlers may come into contact with the contaminated fluids contained in the canisters due to spillage, leaks or splashing while carrying, emptying or cleaning the canisters.

In an effort to minimize exposure to pathogens in the aspirated fluid, the canisters may be partially pre-filled with a disinfectant to destroy any pathogens as the fluid enters the canisters. Alternatively solidifying agents or coagulants may be added to the canisters to minimize the potential for spillage, splashing and leakage. However, such additives increase the disposal costs because the canisters must then be treated as hazardous waste and must be incinerated or delivered to a landfill. Furthermore, there is also the additional labor and associated costs with having to purchase, store, and handle the canisters themselves. In any event, whether disinfectants or solidifiers are added, there remains a risk that handlers of the canisters will still come into contact with the fluid waste.

In an attempt to overcome the risk of exposure to pathogens and the additional costs and labor associated with the use of canisters to collect fluid waste, systems have been developed to collect the fluid waste in reservoirs which can be drained directly into the facility's sewer system. However, such systems operate in a manner very similar to the canister systems (apart from having to handle the canisters). Specifically, such systems utilize redundant reservoirs and piping so that when the first reservoir is filled, the operator has to manually disconnect the suction hose from the first reservoir and re-connect the suction hoses to the second reservoir which presents the same undesirable interruption of the medical procedure as when using a canister-type collection system.

In an attempt to minimize the interruption of the medical procedure, others have attempted to automate the process using redundant systems, with each system having its own reservoir, vacuum line, drain pipe, fluid level sensor and associated valving. In use, the first reservoir is under negative pressure and collects the fluid. When the first reservoir reaches a predetermined fill level as detected by the first fluid level sensor, the system is programmed to switch the negative pressure from the first reservoir to the second reservoir, such that the second reservoir begins to collect the fluid while the fluid in the first reservoir is drained. This automatic switching between filling and draining the redundant systems is repeated until the medical procedure is completed. While the switching between reservoirs is much quicker using the automated process than doing so manually, and while the capacity to collect fluid is theoretically unlimited, such automatic switching systems nevertheless still cause an undesirable brief interruption of the suction while the system switches between the reservoirs.

Accordingly, there remains a need for an efficient system for collecting and disposing of aspirated fluid waste from medical procedures, which eliminates the need for handling of canisters to avoid the potential risk of exposure to pathogens, which has an unlimited capacity, and which avoids any interruption of suction during the medical procedure.

DESCRIPTION

Figure 1:
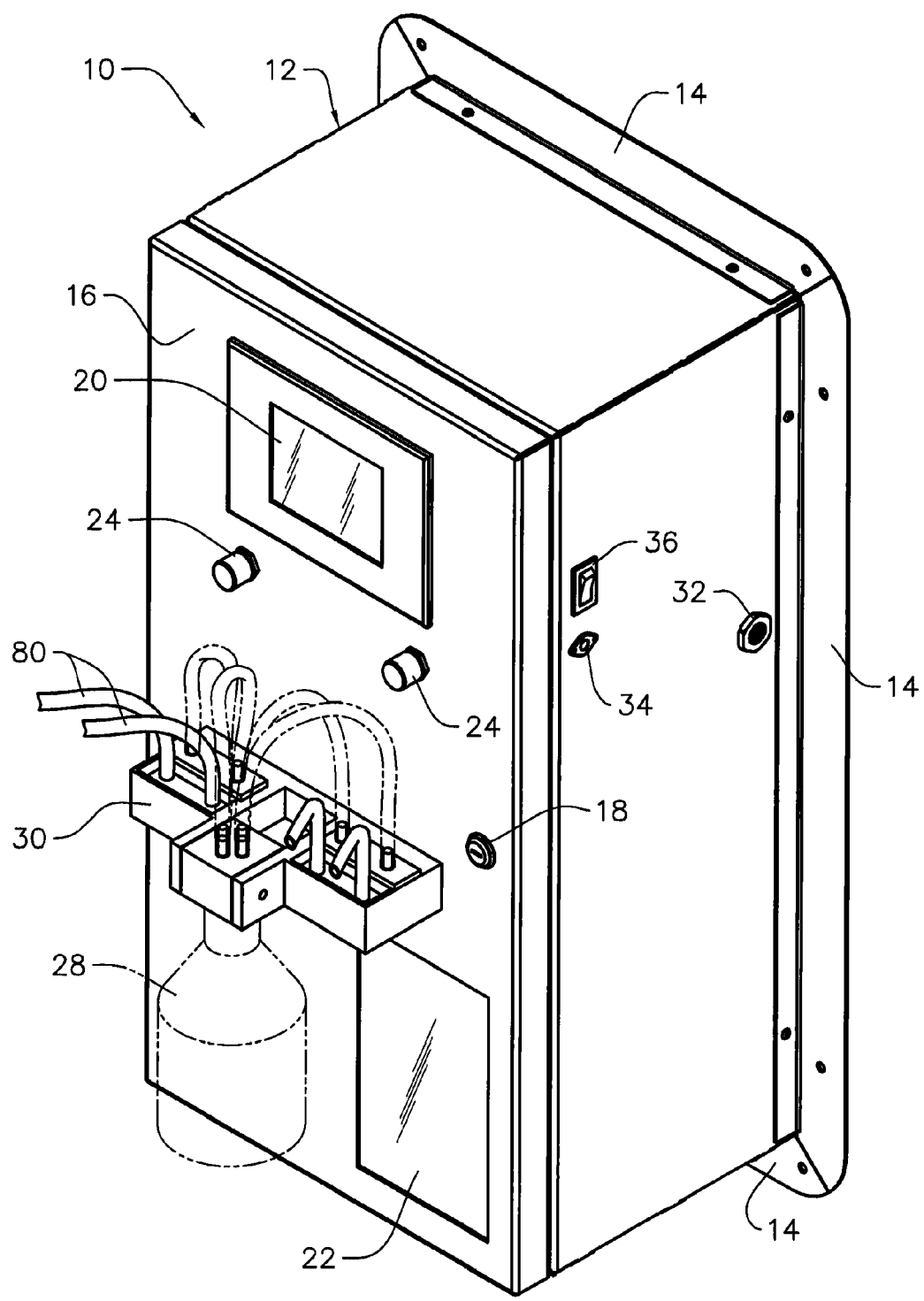
FIG. 1 is a top perspective view of one embodiment of a housing and manifold for a fluid waste collection and disposal system.
Figure 2:
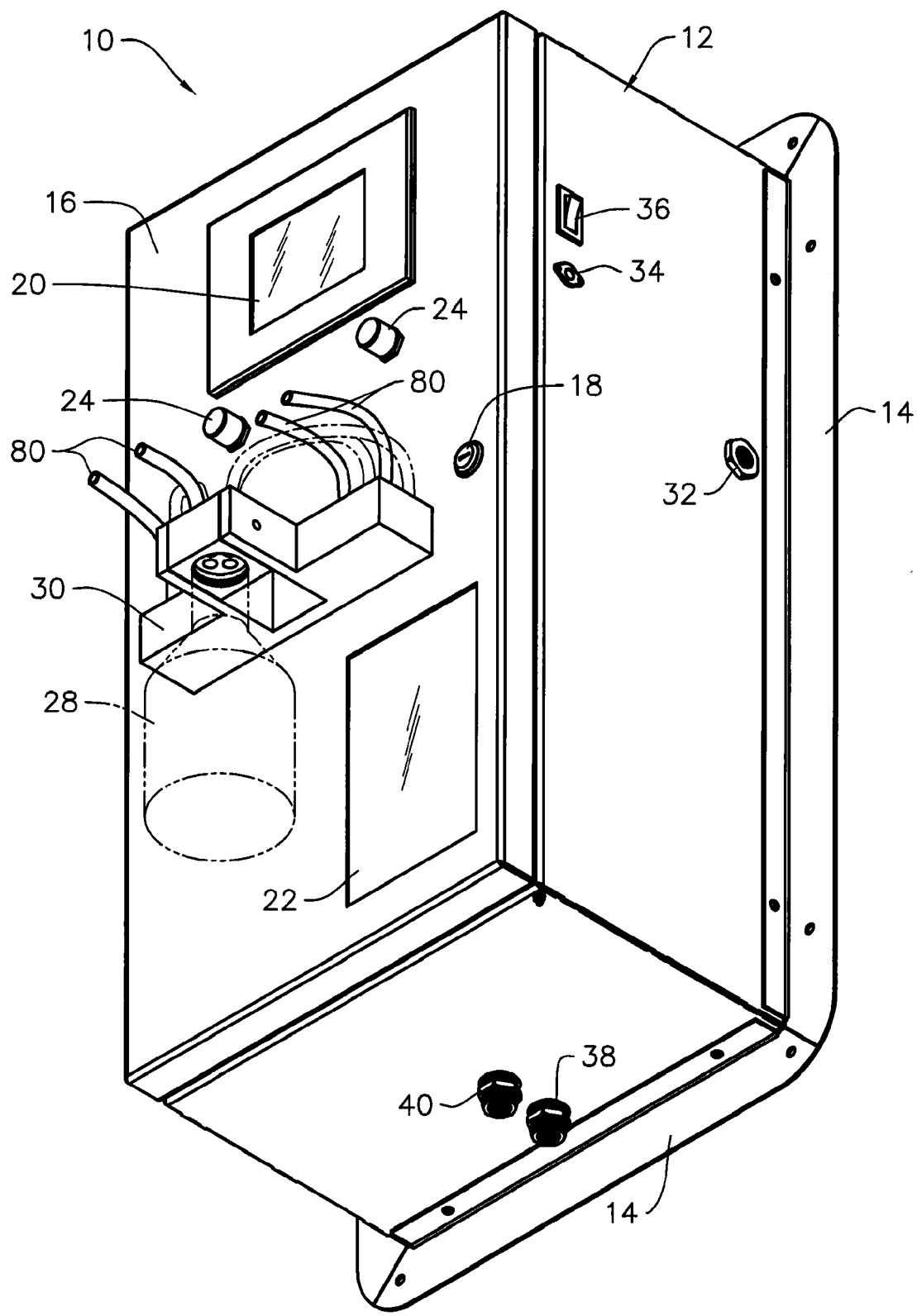
FIG. 2 is a bottom perspective view of the housing of the fluid waste collection and disposal system of FIG. 1.

Referring now to the drawings, wherein like reference numerals designate identical or corresponding parts throughout the several views, FIGS. 1 and 2 are top and bottom perspective views, respectively, of an embodiment of a fluid waste collection and disposal system designated generally by reference numeral 10. The system 10 is shown having a housing 12 adapted for mounting on a wall or in a partially recessed fashion into a wall in the operating room or other facility in which fluid aspiration procedures are performed. A mounting flange 14 is provided for securing the housing to any suitable surface or structure using appropriate fasteners. It should be appreciated, however, that the system 10 may be a free standing stationary or portable system.

The housing 12 includes a front panel 16 for access to the interior of the housing and the components therein (discussed later). The front panel 16 may include a lock 18 or other security mechanisms to prevent unauthorized access to the interior of the housing 12. The front panel 16 includes a touch screen display 20, a fluid viewing window 22, and one or more vacuum adjustment controllers 24. The vacuum adjustment controller(s) 24, may be rotatable dials, push buttons, slide mechanisms or part of the touch screen display 20. As discussed in more detail later, the front panel 16 also supports a manifold 30 comprising plurality of suction ports to which suction hoses 80 are attached. The manifold 30 may support a cleaning solution hanger (discussed later) for removably receiving a cleaning solution bottle 28. One side panel of the housing 12 may include a vacuum connection port 32, a power source connection 34 and an on-off switch 36. The power source may be 24 Volt DC or any other suitable power source. A bottom panel of the housing 12 may include a main drain port 38 and a secondary drain port 40. It should be appreciated that the particular location of the foregoing items may vary depending on the configuration of the housing and the components therein and where and how the system 10 is installed and/or mounted.

Figure 3A:
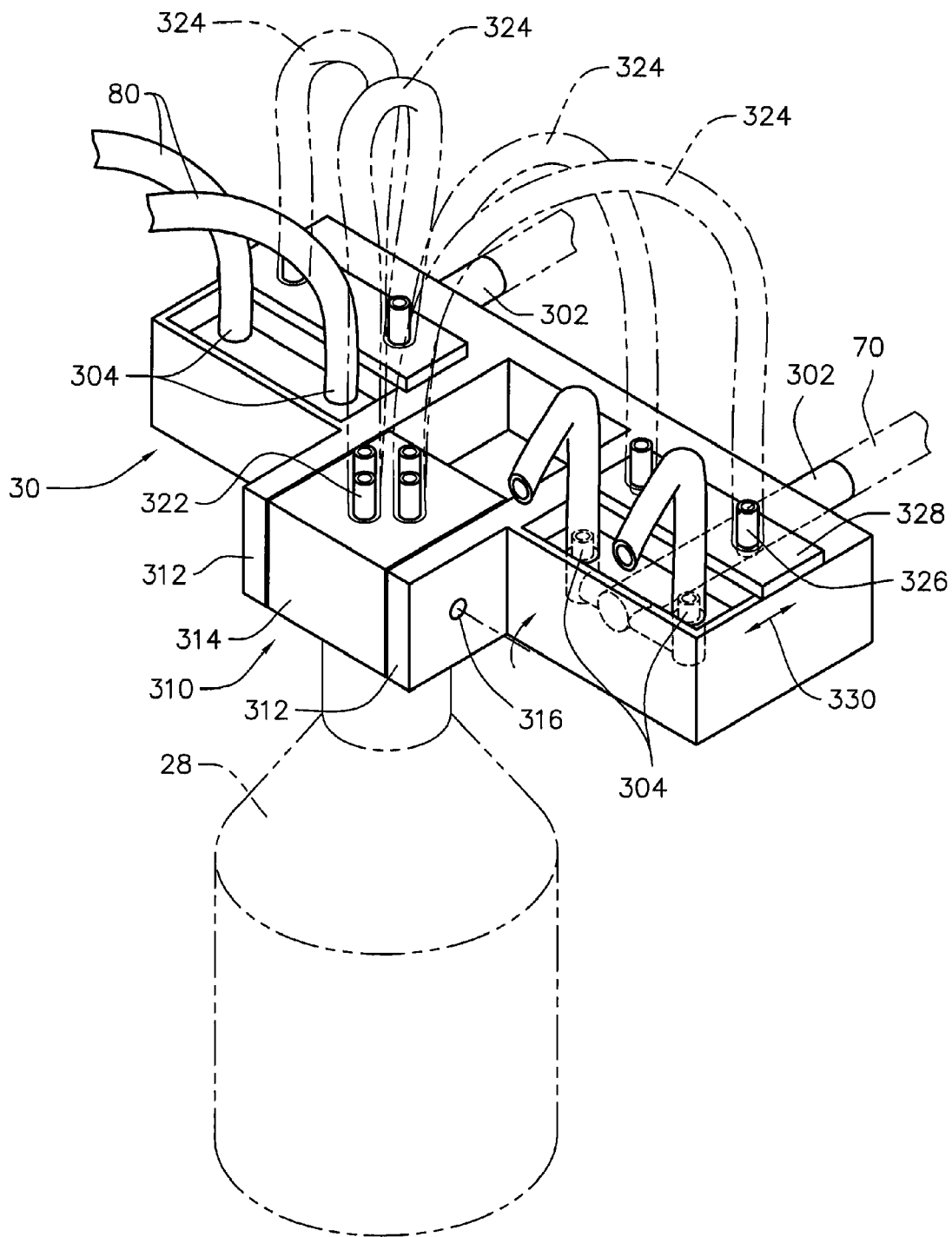
FIGS. 3A and 3B are enlarged perspective views of the manifold of FIG. 1 showing the cleaning solution hanger in an attachment position and in an inverted use position.
Figure 3B:
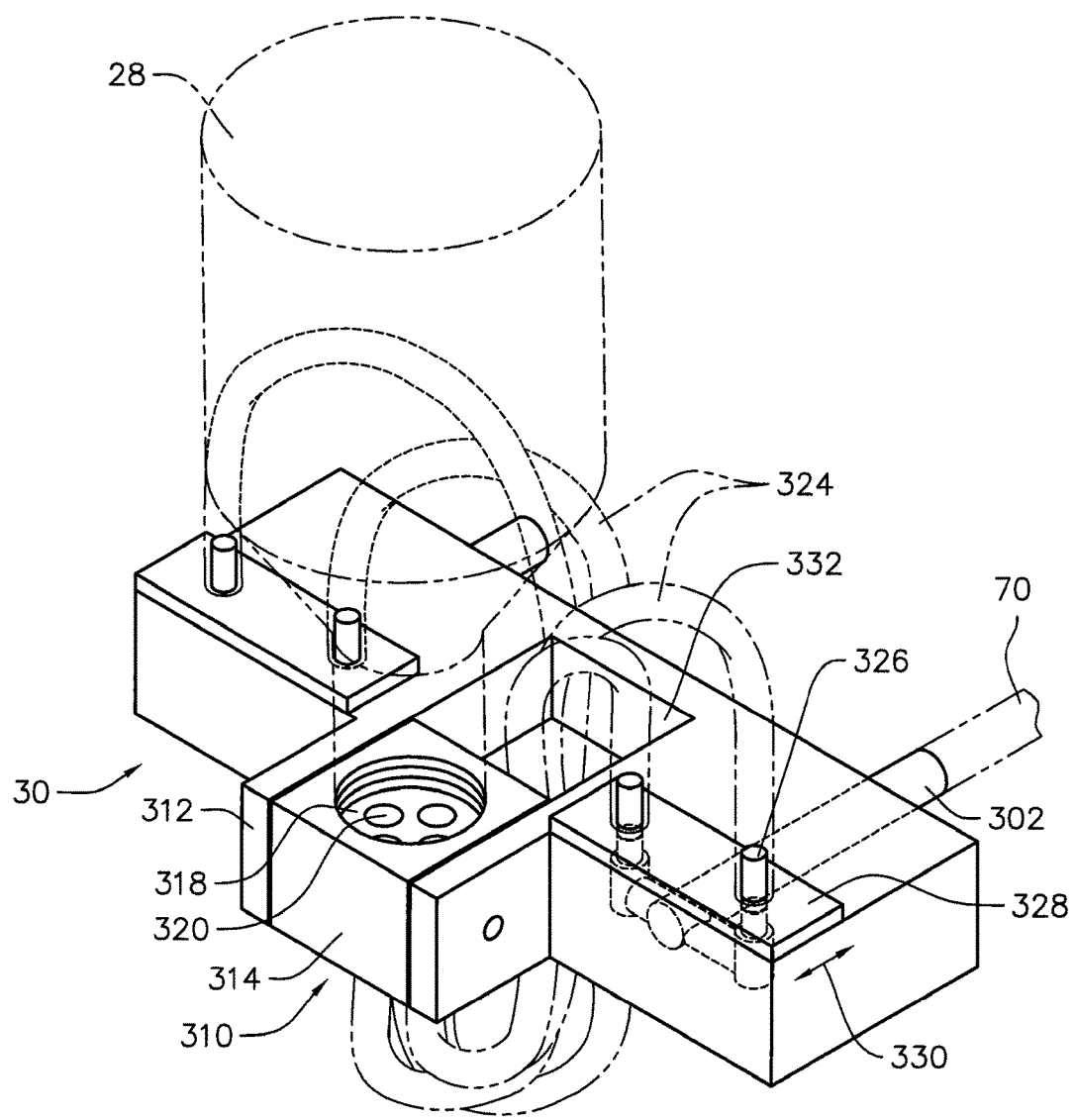

FIGS. 3A and 3B are enlarged perspective views of the manifold 30 of FIG. 1. The manifold 30 includes outlet ports 302 which connect to the fluid inlet line 70. Each of the outlet ports 302 are in fluid communication with a pair of suction ports 304 to which the suction hoses 80 attach as shown in FIG. 3A. It should be appreciated that rather than connecting the suction hoses 80 to the suction ports 304 directly, the suction hoses 80 may connect to a filter (not shown) which then connects to the suction ports 304. The manifold 30 also supports a cleaning solution hanger 310, which includes outwardly projecting arms 312 which support a block 314 rotatable about a pin 316. One end of the block includes a threaded receptacle 318 (FIG. 3B) for threadably receiving a threaded end of a cleaning solution bottle 28. After threading the bottle 28 to the block 314, the bottle 28 and block 314 may be rotated such that the bottle 28 is inverted with respect to the manifold 30 as shown in FIG. 3B. Passages 320 (FIG. 3B) communicate the cleaning solution from the inverted bottle 28 through the block 314 and through nipples 322 on the opposite side of the block 314. Cleaning solution tubes 324 are connected at one end to the nipples 322 on the block 314 and are connected at the other end to nipples 326 on a door 328 that is slidable as indicated by arrow 330. As shown in FIG. 3B, when the bottle 28 is inverted, the cleaning solution tubes 324 pass through an opening 332 in the manifold 30. Also as shown in FIG. 3B, during the Cleaning Cycle Process (described later), the suction hoses 80 (or filter, if used) are disconnected from the suction ports 304 and door 328 is moved to the closed position such that the door nipples 326 are aligned with the suction ports 304. An o-ring may be provided on the underside of the door 328 around the openings of the door nipples 326 to provide a fluid-tight connection between the door nipples 326 and the suction ports 304. A switch (not shown) may be provided in the hanger 310 such that when the block 314 and bottle 28 are inverted, a signal is generated permitting the cleaning process to continue. It should be appreciated, that instead of using a manifold 30, one or more suction ports 304 may be provided in the face of the panel 16 which connect to the fluid inlet line 70. In such an embodiment, the suction hoses 80 (and/or filter) may be connected directly to the panel suction ports 304 (see FIG. 10). Similarly, the cleaning solution tubes 324 may be connected directly to the suction ports 304 after removal of the suction hoses 80 from the panel suction ports 304.

The system 10 includes a programmable logic controller ("PLC") (not shown) which interfaces with the touch screen display 20 and other circuitry. The circuitry and associated programming for the PLC for providing the features and performing the functions described below in connection with the "Fluid Collection and Disposal Process" and "Cleaning Cycle Process" would be readily understood and recognized by those skilled in the art and therefore further discussion on the circuitry is not warranted. Rather than using a PLC and associated circuitry, it should be appreciated that solid state circuitry could be utilized which could further reduce the total size of system 10, if desired, as well as provide additional desired functionality.

Figure 4:
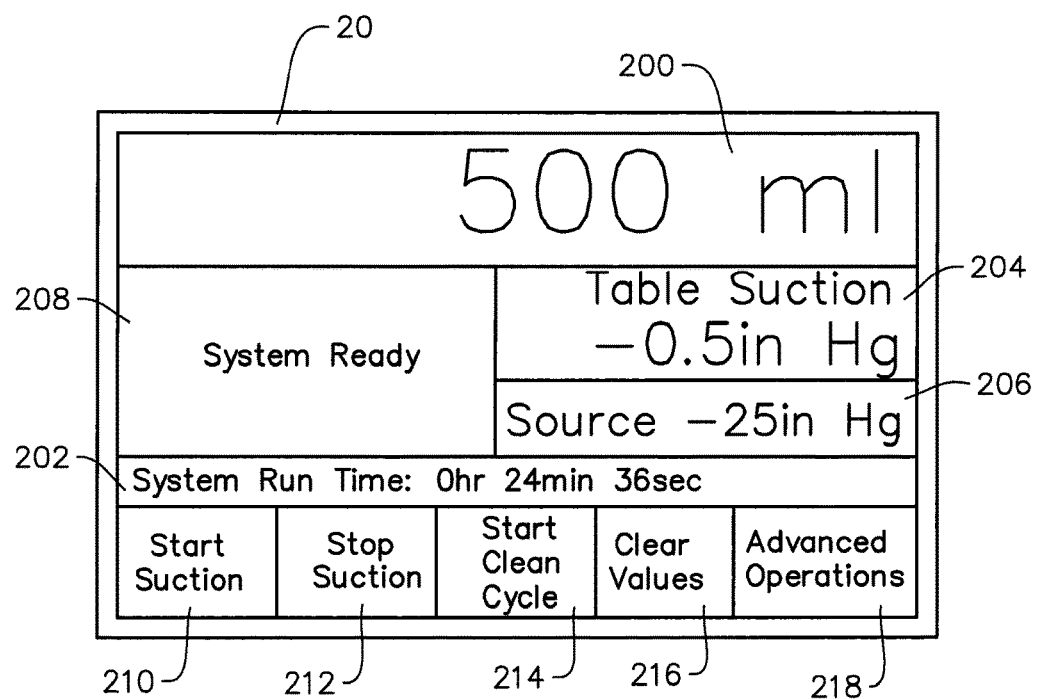
FIG. 4 illustrates an embodiment of a touch screen display of the fluid waste collection and disposal system of FIG. 1.

In FIG. 4, an embodiment of a display screen is illustrated for the touch screen display 20. As illustrated, the touch screen display 20 includes a "Fluid Collected" indicator 200, a "System Run Time" indicator 202, a "Table Suction" indicator 204, a "Source Suction" indicator 206, a status/information indicator 208, and a plurality of selectable operational functions, including a "Start Suction" selection 210, a "Stop Suction" selection 212, a "Start Clean Cycle" selection 214, a "Clear Values" selection 216 and an "Advanced Operations" selection 218. The Fluid Collected indicator 200 indicates the volume of fluid collected (preferably in milliliters) since pressing the Start Suction selection 210. The System Run Time indicator 202 indicates the time passed, preferably displayed in hours, minutes and seconds, since pressing the Start Suction selection 210. The Table Suction indicator 204, indicates the vacuum or negative pressure, preferably in inches or mm Hg, at the suction ports 304 which is controlled by the vacuum adjust controller 24 on the front panel 16. If multiple suctions ports 304 are provided, a separate Table Suction indicator 204 may be provided to indicate the negative pressure at each suction port. The Source Suction display 206, indicates, the suction provided by the facility's vacuum system, preferably in inches or mm Hg, to which the vacuum port 32 is connected. The status/information indicator 208 provides information to the operator such as the current operation selection, system status or any alarm conditions.

FIGS. 5-10 schematically illustrate alternative embodiments of the fluid waste collection and disposal system 10. In each of the embodiments, the system 10 includes first and second reservoirs 50, 52, a conduit 54, fluid transfer valve 56, a drain pipe 58, a fluid discharge mechanism 59, a fluid sensor 60, a fluid inlet line 70, an inlet line valve 72, a vacuum line 90, a vacuum line valve 92, an auxiliary line 100, an auxiliary line valve 102 and a recirculation line 150. In the different embodiments, additional lines and valves or different combinations thereof, cooperate to control air flow and/or fluid flow through the system 10 as described in detail later under the "Fluid Collection and Disposal Process".

In each of the embodiments, the first reservoir 50 is fluidly connected to the second reservoir 52 by the conduit 54. The fluid transfer valve 56, is disposed along the conduit 54 to control the transfer of collected waste fluid from the first reservoir 50 to the second reservoir 52 (discussed later). The fluid transfer valve 56 may be a solenoid or motor driven valve, a check valve or other suitable valve. The drain pipe 58 is connected to the second reservoir 52 through which the collected fluid waste is discharged from the second reservoir 52 into a suitable drain or waste pipe (not shown) for disposal. The fluid discharge mechanism 59 is disposed along the drain pipe 58 to control the discharge of the collected fluid waste from the second reservoir 52 into the drain or waste pipe. The fluid discharge mechanism 59 may be an electronically controllable valve, such as a solenoid or motor driven valve, or a check valve or other suitable valve. Alternatively, the fluid discharge mechanism 59 may comprise a pump or the combination of a valve and pump.

Figure 5:
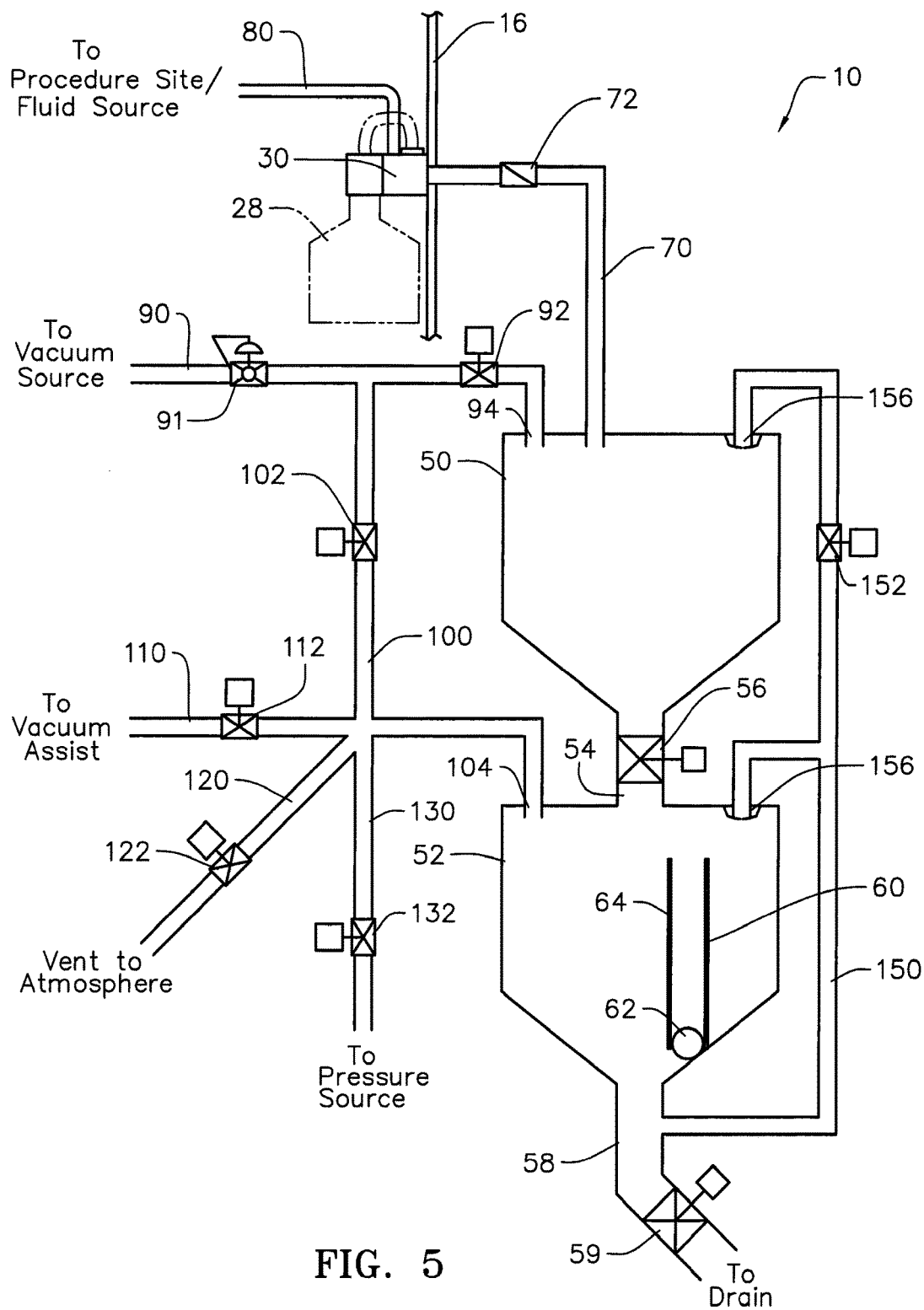
FIGS. 5-9 schematically illustrate alternative embodiments of the fluid waste collection and disposal system wherein the fluid reservoirs are shown in stacked relation.
Figure 6:
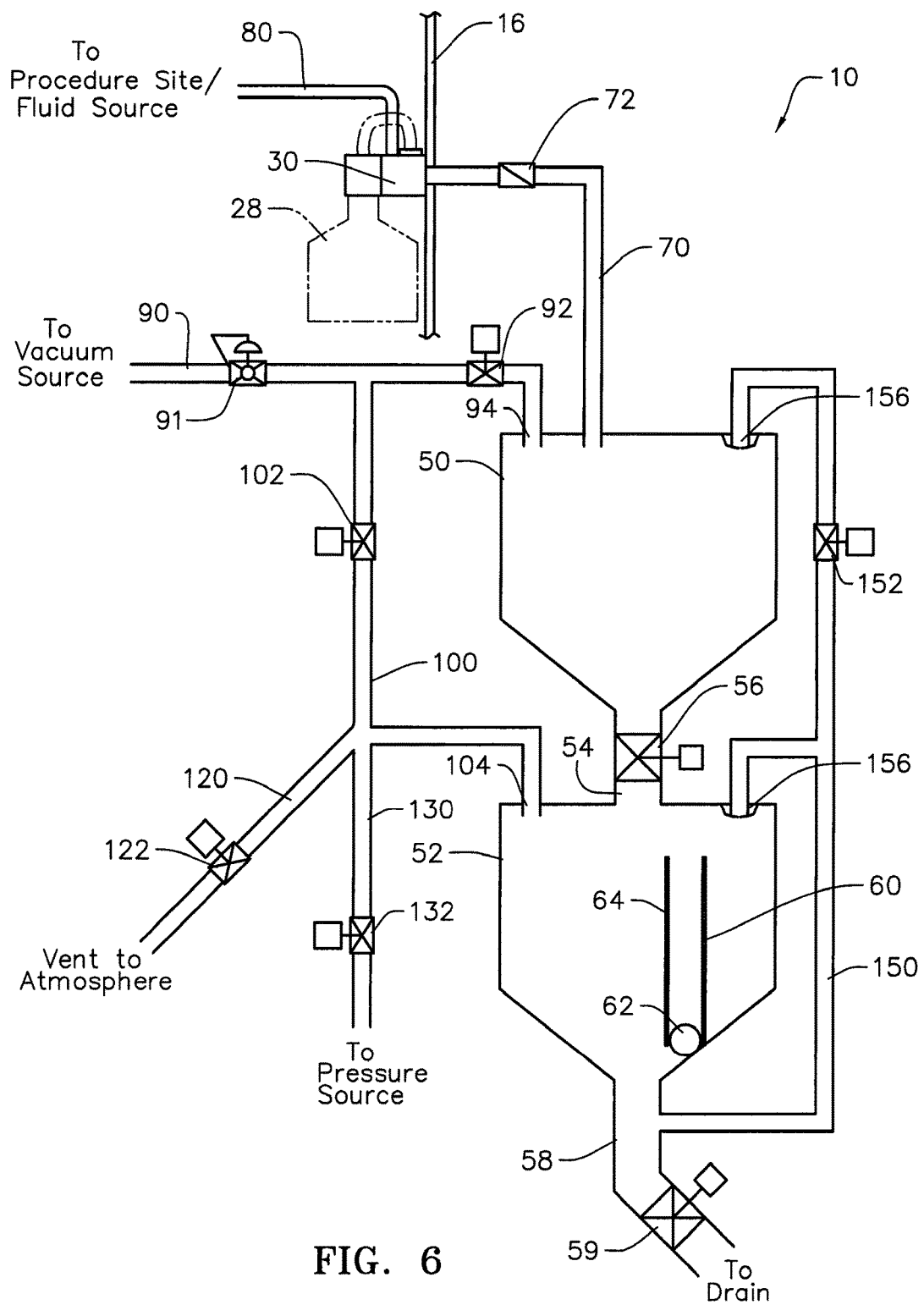
Figure 7:
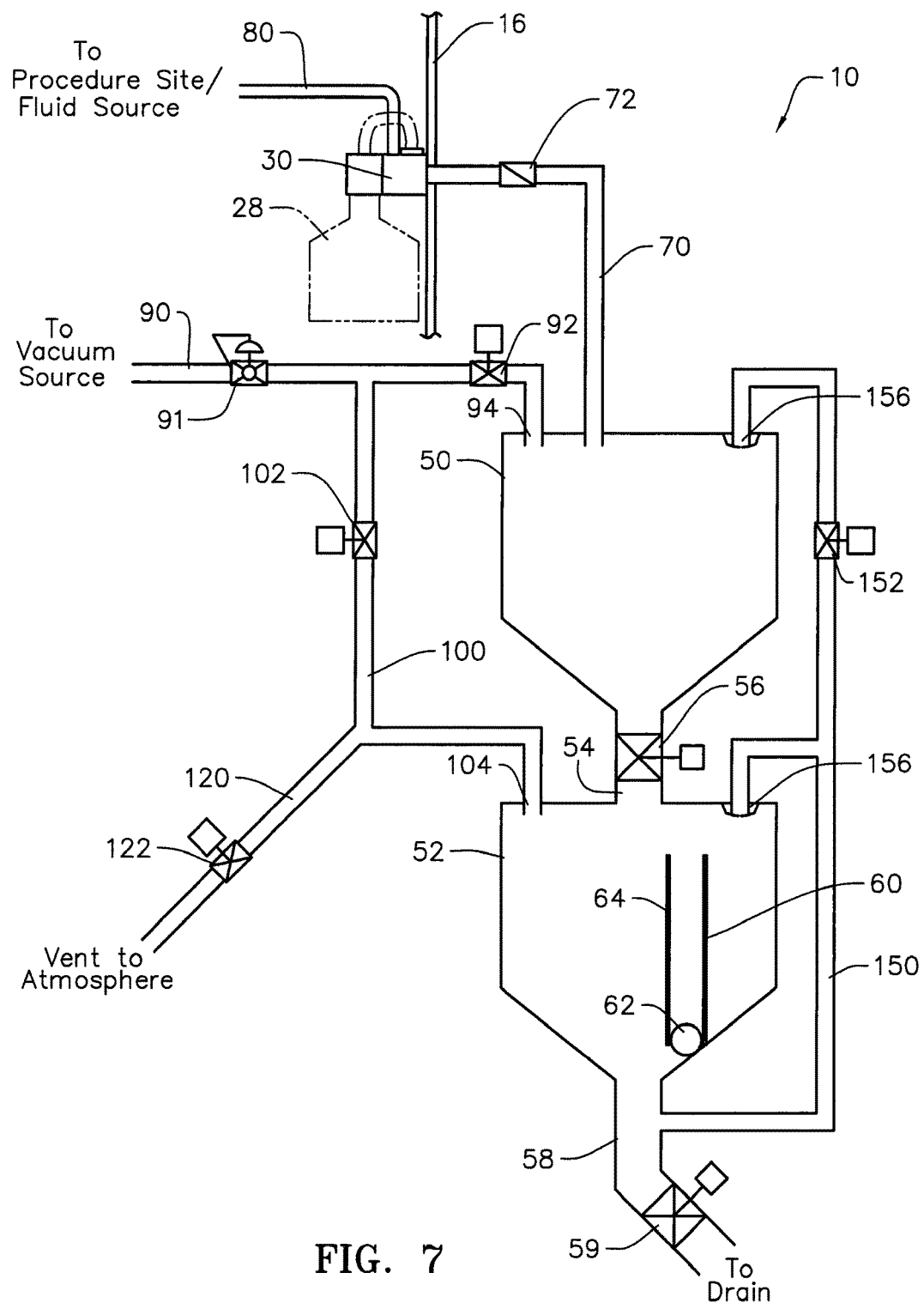

The fluid sensor 60 is disposed to detect the amount of fluid collected from the patient or fluid source during the procedure. The fluid sensor 60 may be a mechanical float-type sensor, such as a ball-float sensor, or the fluid sensor 60 may be an electronic sensor such as a capacitive sensor, an optic sensor, an ultrasonic sensor, a piezo-resistance sensor, or the fluid sensor 60 may be a mass/weight measuring sensor, such as a load cell or the fluid sensor 60 may be a flow sensor, such as a flow meter disposed in the fluid inlet line 70, or any other suitable sensor for detecting the volume, level or mass/weight of the fluid collected from the fluid source during the procedure. In the embodiment of FIGS. 5-7, the fluid sensor 60 is shown as a ball-float sensor disposed within the second reservoir 52. In this embodiment, a ball 62 floats up and down within a sensor tube 64 to activate switches (not shown) depending on the fluid level in the second reservoir 52. In the embodiment illustrated in FIG. 8, the fluid sensor 60, is shown as comprising an electronic sensor. In this embodiment, the fluid sensor 60 comprises a low level sensor 66 and a high level sensor 68 disposed in the second reservoir 52. In the embodiment illustrated in FIG. 9, the fluid sensor 60 is shown as a load cell (designated by arrows) to detect the mass/weight of the fluid in the first and second reservoirs. In the embodiment of FIG. 10, the fluid sensor 60 is shown as a flow meter to detect the volume of fluid passing through the fluid inlet line 70. It should be appreciated that if a load cell or other mass/weight measuring sensor is used, the reservoir supports within the housing, as well as the conduit 54, drain pipe 58 and other components may need to be flexible so the mass/weight of the fluid can be accurately detected or determined.

The fluid inlet line 70 is fluidly connected at one end to the manifold 30 and at its other end to the first reservoir 50. The inlet line valve 72, such as a check valve, is positioned along the fluid inlet line 70. On the exterior of the housing 12, single use disposable suction hoses 80 connect to the suction ports 304 in the manifold 30. Rather than connecting the suction hoses 80 directly to the suction ports 304, a single use disposable filter 76 may be inserted into the suction ports 304 and the suction hoses may be attached to the filter. An end effector (not shown) on the distal end of the suction hose 80, is used to suction or aspirate the waste fluid from the patient.

The vacuum line 90 extends between a regulated vacuum source (not shown) and a vacuum port 94 of the first reservoir 50. Disposed along the vacuum line 90 is the regulator 91 and the electronically controllable vacuum line valve 92, such as a solenoid or motor driven valve. The auxiliary line 100 branches off the vacuum line 90 and connects to an auxiliary port 104 of the second reservoir 52. Disposed along the auxiliary line 100 is the electronically controllable auxiliary line valve 102, such as a solenoid or motor driven valve.

Recirculation lines 150 and an electronically controllable valve or one or more recirculation pumps are provided for recirculating cleaning solution during the "Cleaning Cycle Process" (described later).

The various embodiments illustrated in FIGS. 1-10 are hereinafter described. In the embodiment of FIG. 5, the fluid transfer valve 56 and the fluid discharge mechanism 59 comprise electronically controllable valves as previously described. In addition to the components identified above which are common among all the embodiments, the embodiment of FIG. 5 also includes a vacuum assist line 110 connecting a vacuum assist source (not shown) to the auxiliary line 100. Disposed along the vacuum assist line 110 is an electronically controllable vacuum assist line valve 112, such as a solenoid or motor driven valve. A vent line 120 which vents to atmosphere also connects to the auxiliary line 100. Disposed along the vent line 120 is an electronically controllable vent line valve 122 such as a solenoid or motor driven valve. Additionally, a pressure line 130 connects a pressure source, such as an air compressor (not shown) to the auxiliary line 100. Disposed along the pressure line 130 is an electronically controllable pressure line valve 132 such as a solenoid or motor driven valve. Also in the embodiment of FIG. 5, the recirculation line 150 fluidly connects the first and second reservoirs 50, 52 and an electronically controllable valve 152 is disposed along the recirculation line 150 to control the flow of cleaning solution during the Cleaning Cycle Process.

The embodiment of FIG. 6 is substantially the same as FIG. 5 except that the vacuum assist and associated vacuum assist line 110 and vacuum assist line valve 112 are eliminated.

The embodiment of FIG. 7 is likewise substantially similar to FIG. 5 except that the vacuum assist and pressure source and associated lines 110, 130 and valves 112, 132 are eliminated.

Figure 8:
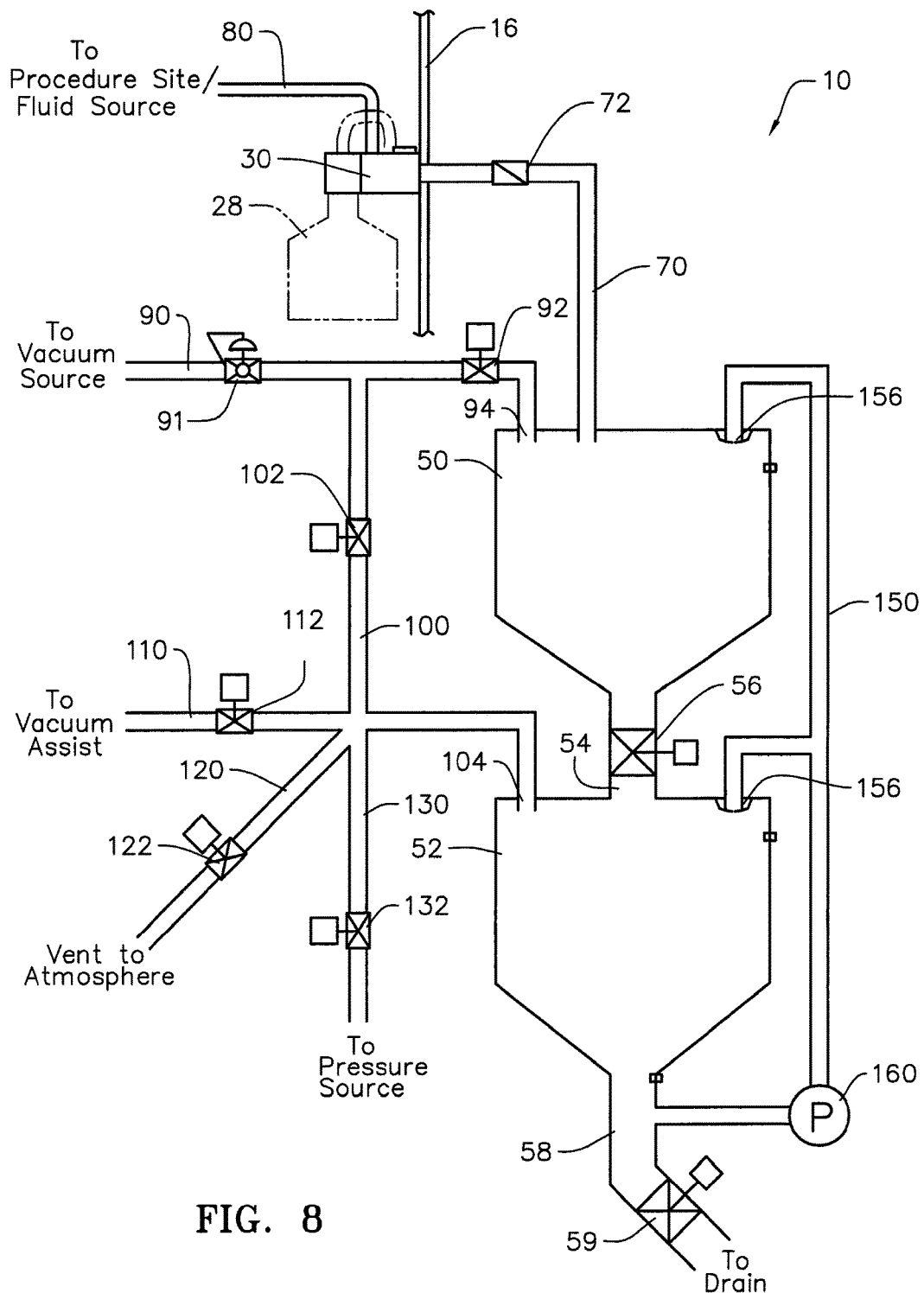

The embodiment of FIG. 8 is substantially the same as FIG. 5, except that a recirculation pump 160 rather than the recirculation line valve 152 is used to control the flow of cleaning solution during the Cleaning Cycle Process.

Figure 9:
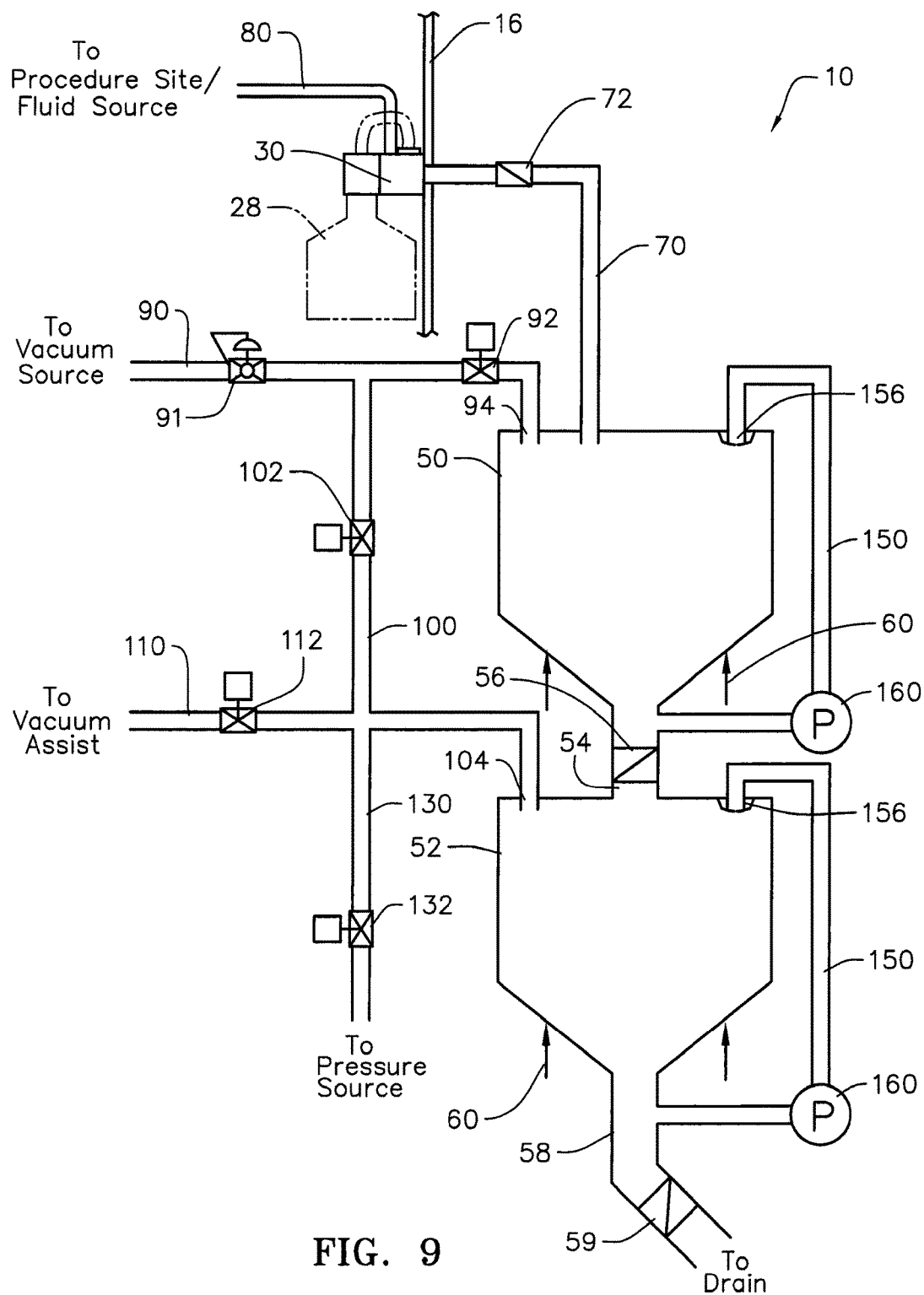
Figure 10:
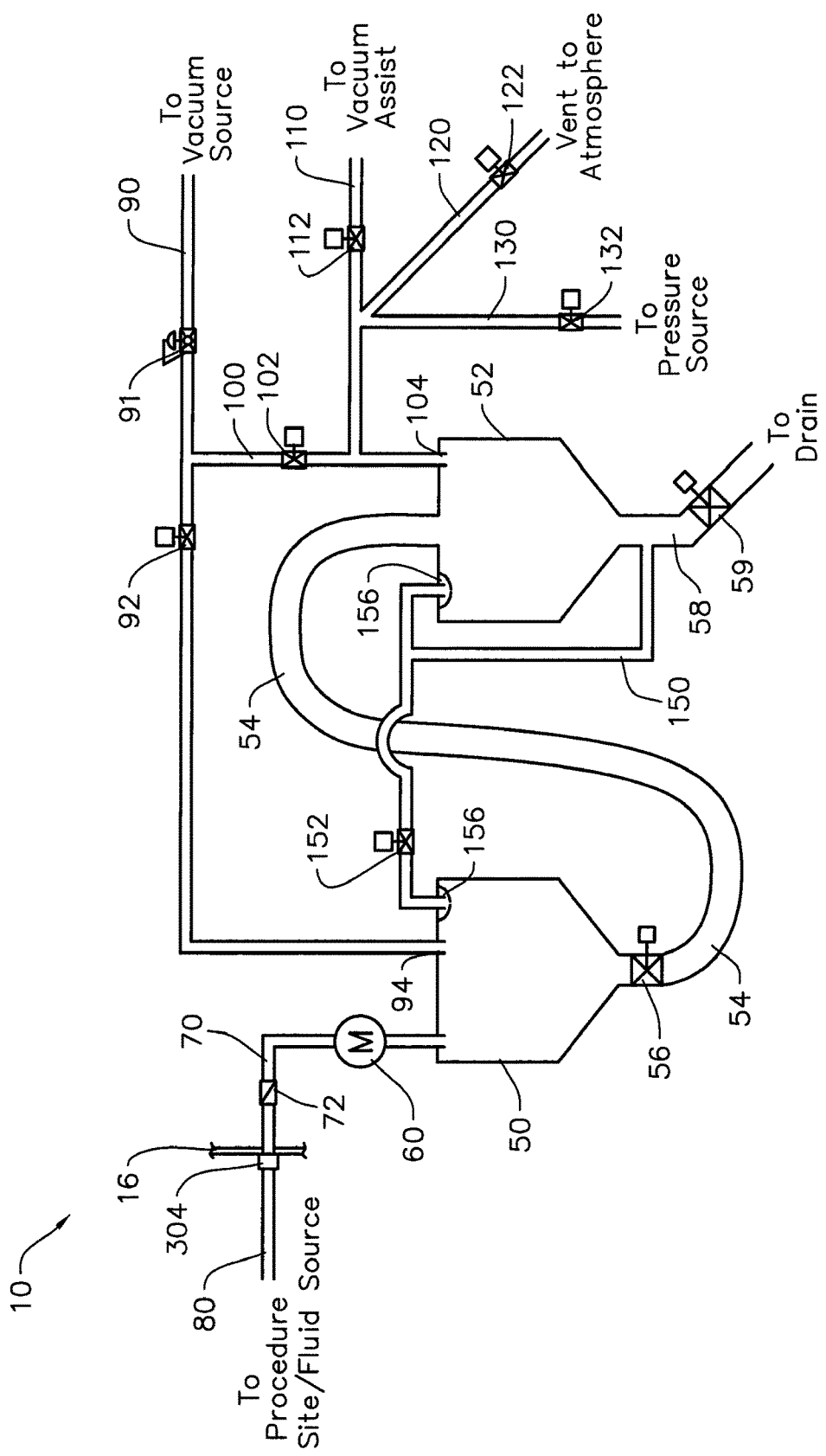
FIG. 10 schematically illustrates another embodiment of a fluid waste collection and disposal system with the fluid reservoirs in a side-by-side relation.

In the embodiment of FIG. 9, the fluid transfer valve 56 and fluid discharge mechanism 59 comprise check valves. Additionally, the vent line 120 and associated vent line valve 122 are eliminated. Also in the embodiment of FIG. 9, separate recirculation lines 150 and separate recirculation pumps 160 are used to control the flow of cleaning solution during the Cleaning Cycle Process.

The embodiment of FIG. 10, is substantially the same as the embodiment of FIG. 5, except that the first and second reservoirs 50, 52 are arranged in a side-by-side relationship as opposed to a stacked relationship.

Although not shown, corresponding embodiments to those of FIGS. 6-9 may also be utilized for the embodiment of FIG. 10 where the reservoirs 50, 52 are arranged in the side-by-side relation. It should also be appreciated that the various components of the different embodiments identified above may be interchangeable among the embodiments and arranged in various configurations.

The first and second reservoirs 50, 52 and associated components in the various embodiments are constructed of suitable material of sufficient thickness to safely withstand the negative pressures typically used for the vacuum systems of a medical facility, which typically are not greater than 25 inches (635 mm) of mercury (Hg). Additionally, the reservoirs and associated components are preferably designed to withstand positive pressures of up to 20 psi. A suitable material for the reservoirs may be transparent acrylic to allow the surgeon or other medical personnel to view the aspirated fluid as it is collected for assessing its color or other characteristics. The first and second reservoirs 50, 52 are preferably configured with sloped bottom walls to permit the complete drainage of collected waste fluid as discussed in detail later.

A light strip (not shown) which may comprise a plurality of white light emitting diodes (LEDs) may be disposed behind the reservoirs 50, 52 to back-light the fluid in the reservoirs 50, 52 so it can be better viewed through the viewing window 22 in the front panel 16. If there is an alarm condition, for example, if there is a leak or if the vacuum has been interrupted due to fluid back-up, the LEDs are preferably caused to light and flash to visually indicate an alarm condition. Under any alarm condition, the PLC is preferably programmed to flash an error message on the touch screen display 20.

Fluid Collection and Disposal Process

The process of collecting and disposing of the fluid waste using the system 10 is described below with reference to FIGS. 11A-11D which correspond to the embodiment of FIG. 5. A brief description of the process for using the embodiments of FIGS. 6-8 and 10 follow the description of the embodiment of FIG. 5. A more detailed discussion of the fluid collection and disposal processes is provided for the embodiment of FIG. 9 with reference to FIGS. 12A-12D in view of the structural and functional difference of the embodiment of FIG. 9 as compared to the other embodiments.

With respect to all the embodiments, the system 10 may be powered on by pressing the on-off switch 36 to the "On" position or, alternatively, by activating the touch screen 20. When the system 10 is powered on or is otherwise activated, the touch screen 20 preferably displays a "system ready" message in the status/information indicator 208 to indicate to the operator that the system is ready for operation.

Fluid in Phase—FIG. 5 Embodiment

Figure 11A:
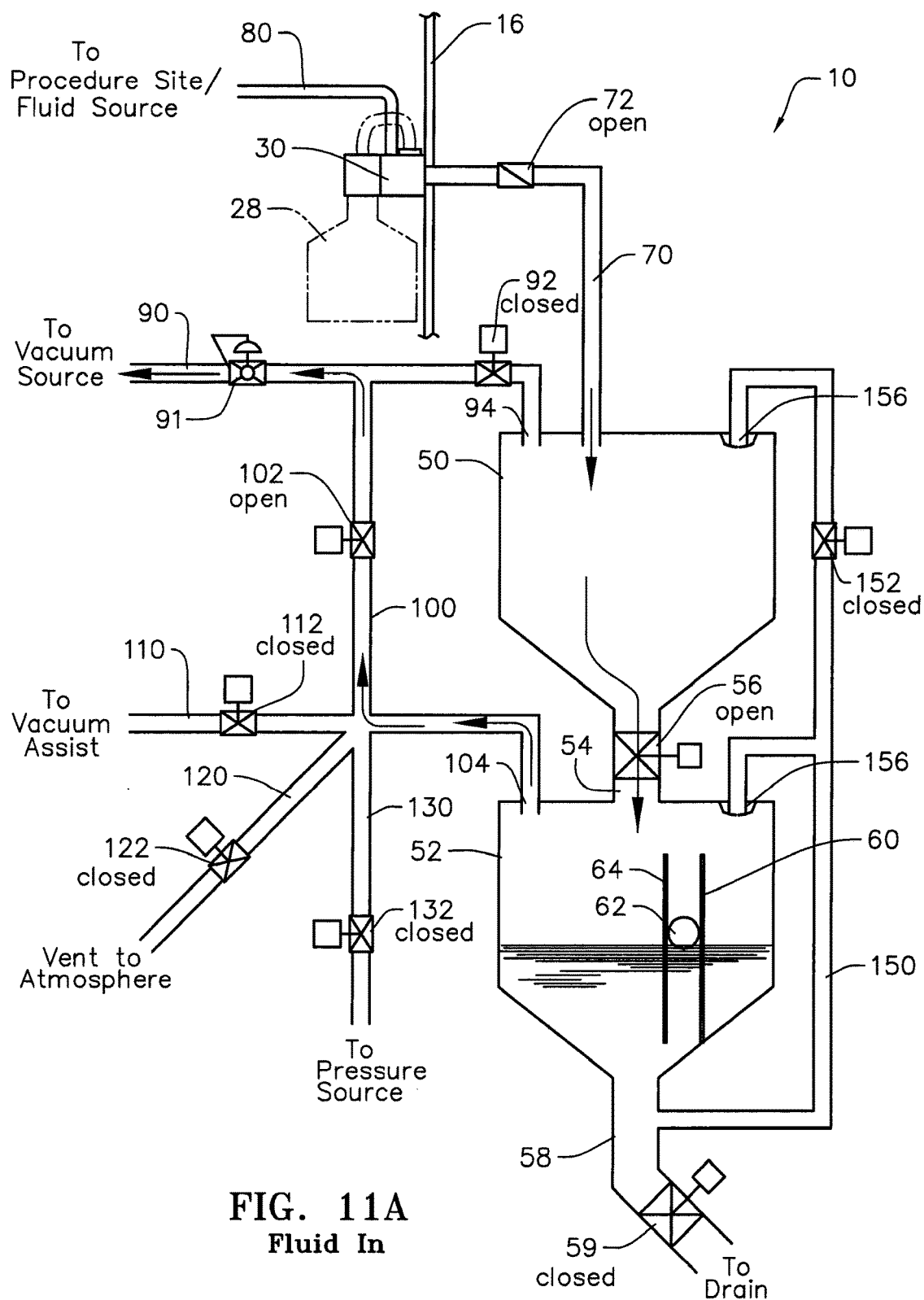
FIGS. 11A-11D schematically illustrate the fluid waste collection and disposal system of FIG. 5 showing various steps of using the system to collect and dispose of fluid waste.

Referring to FIG. 11A, upon selecting the Start Suction operation 210, the initial "Fluid In" phase is initiated by the PLC generating a signal to open the electronically controllable fluid transfer valve 56 and auxiliary line valve 102 permitting communication of the vacuum source with the second reservoir 52, and to the first reservoir 50 through the open fluid transfer valve 56. The electronically controllable valves of the fluid discharge mechanism 59, vacuum assist line valve 112, the vent line valve 122 and the pressure line valve 132 are in the closed position. Because the fluid transfer valve 56 is in the open position, it should be appreciated that the first and second reservoirs 50, 52 will have the same negative pressure due to the air being evacuated (as indicated by the arrows) by the vacuum source. The negative pressure inside the reservoirs 50, 52 creates suction through the inlet line 70, which overcomes the bias of the normally closed inlet line check valve 72, such that suction is provided to the suction ports 304 of the manifold 30.

The operator attaches the suction hose 80 to the suction ports 304. If a filter is used, the filter is connected to the suction ports 304 and the suction hoses are connected to inlets on the filter. The distal end of the suction hose 80 includes an end effector (not shown) which typically includes a regulator for controlling the amount of suction through the end effector. The operator may also adjust the amount of Table Suction 204 using the vacuum adjust controller(s) 24. When the end effector on the suction hose 80 is placed in contact with fluid, fluid is drawn through the suction hose 80 and into the first reservoir 50 and then into the second reservoir 52 due to the fluid transfer valve 56 being open. The fluid entering the first and/or second reservoirs 50, 52 is preferably visible through the window 22 in the front panel. As noted earlier, a light strip may be used to back-light the aspirated fluid entering in the reservoirs so it can be better viewed by the operator.

Relief and Measure Phase—FIG. 5 Embodiment

Figure 11B:
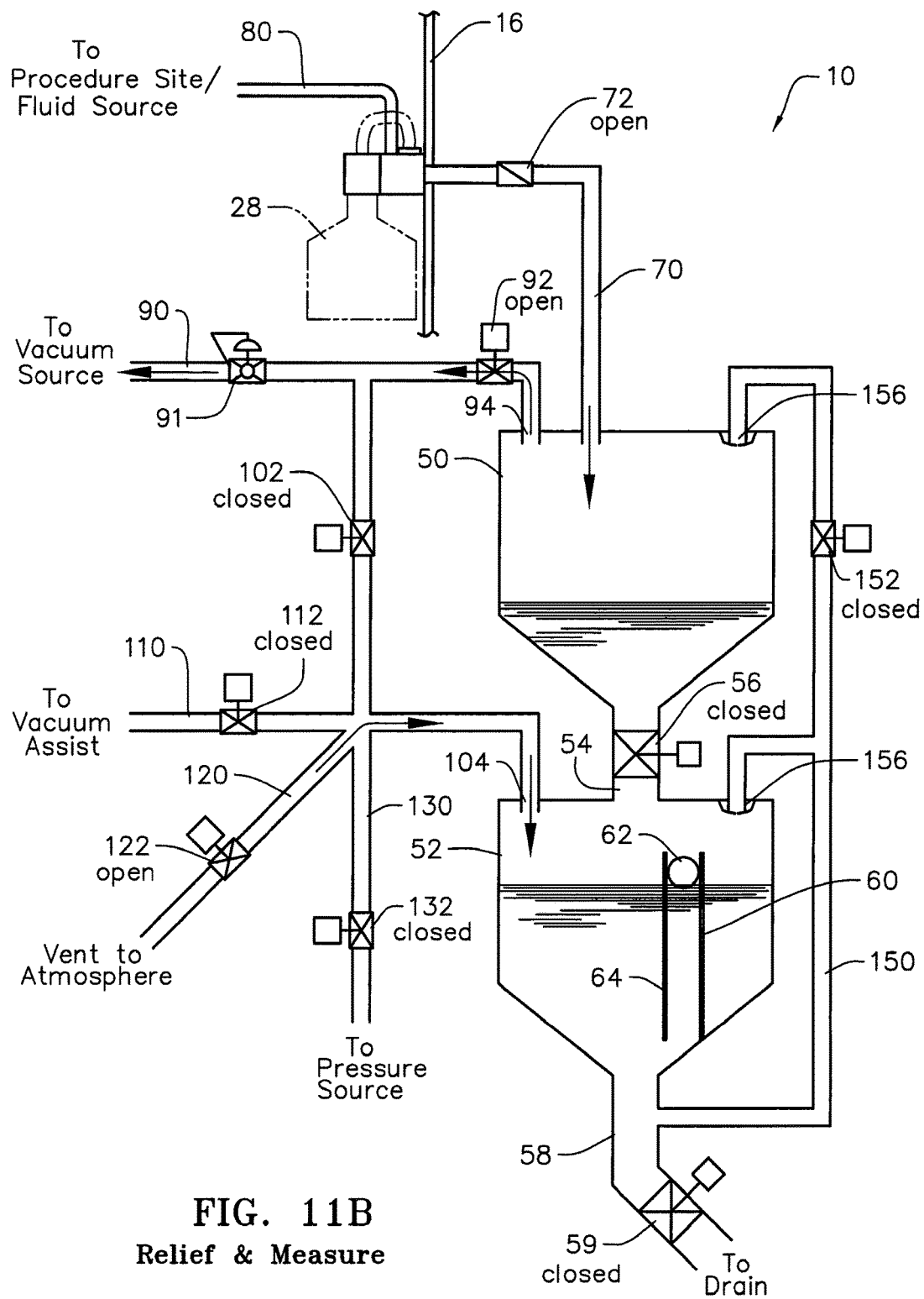

When the fluid level in the second reservoir 52 reaches a predetermined fill level as detected by the fluid sensor 60 (e.g., by the ball float 62 floating upward within the sensor tube 64 until the ball float 62 triggers a switch in the sensor tube 64), a signal is generated which begins the "Relief and Measure" phase as illustrated in FIG. 11B. The generated signal causes the PLC to open the vacuum line valve 92. After the vacuum line valve 92 is opened, the PLC generates a signal to cause the fluid transfer valve 56 and the auxiliary line valve 102 to close, thereby isolating the second reservoir 52 from the vacuum source and the first reservoir 50. It should be appreciated that the first reservoir remains under negative pressure via the open vacuum line valve 92, such that communication of the vacuum source with the first reservoir is not interrupted. When the fluid transfer valve 56 and auxiliary line valve 102 are closed, a signal is generated to cause the PLC to open the vent line valve 122. Upon opening of the vent line valve 122, air enters the second reservoir 52 to relieving the negative pressure until it is brought to atmospheric pressure. The volume of fluid in the second reservoir 52 is then determined or otherwise measured and recorded by the fluid measuring system 400 as described later.

Drain Phase—FIG. 5 Embodiment

Figure 11C:
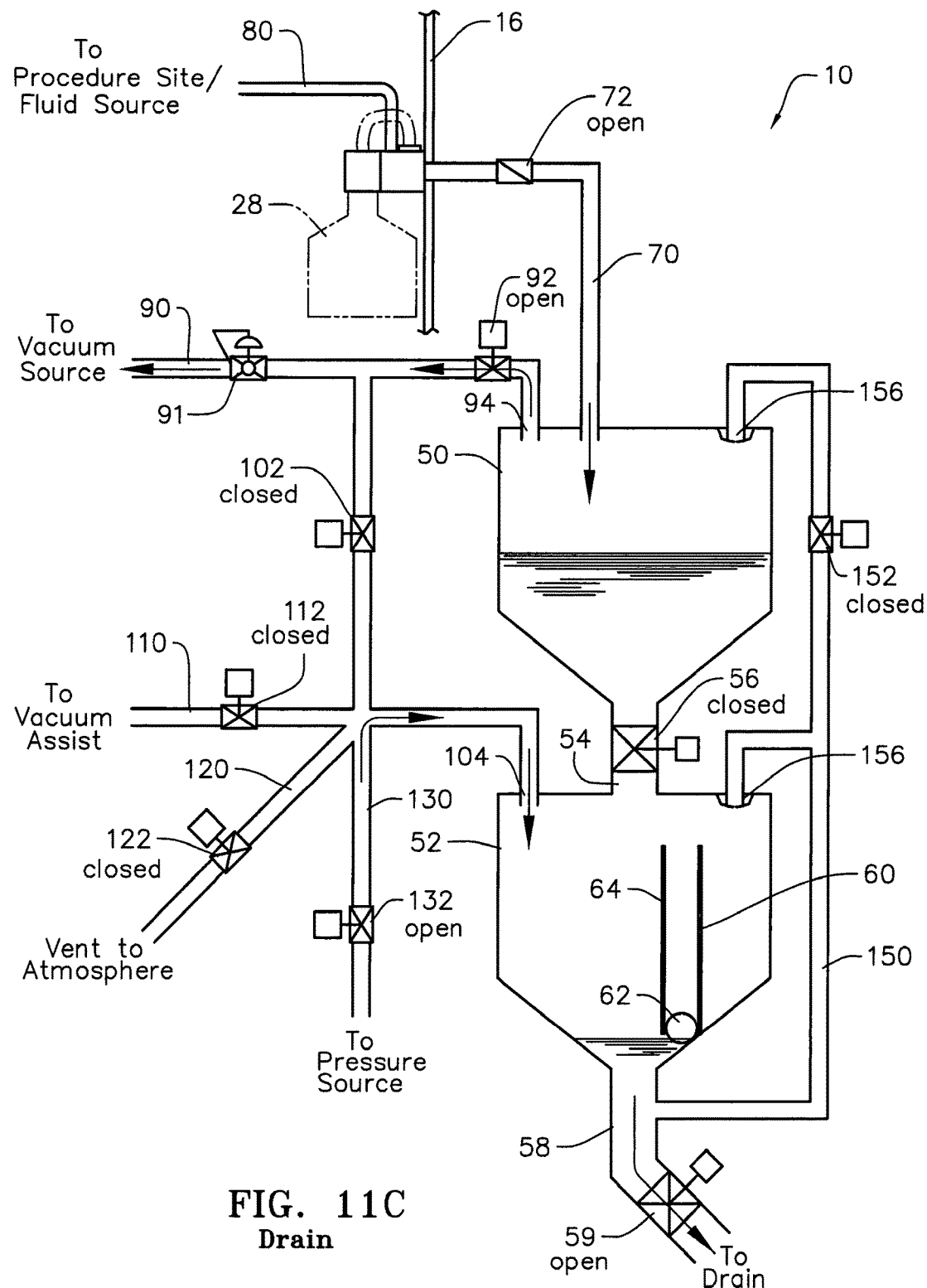

Once the volume of the fluid in the second reservoir has been determined and recorded, the "Drain" phase as illustrated in FIG. 11C is initiated by the PLC generating a signal to cause the electronically controllable valve of the fluid discharge mechanism 59 to open to permit the fluid to begin to drain from the second reservoir 52 via gravity. To more rapidly evacuate the fluid from the second reservoir 52, a signal may be generated by the PLC to cause the vent line valve 122 to close and to cause the pressure line valve 132 to open. With the pressure line valve 132 open, the pressure source, such as compressed air, enters the second reservoir 52 to quickly and completely forcefully evacuate the fluid from the second reservoir 52 through the open valve of the fluid discharge mechanism.

Second Reservoir Preparation Phase—FIG. 5 Embodiment

Figure 11D:
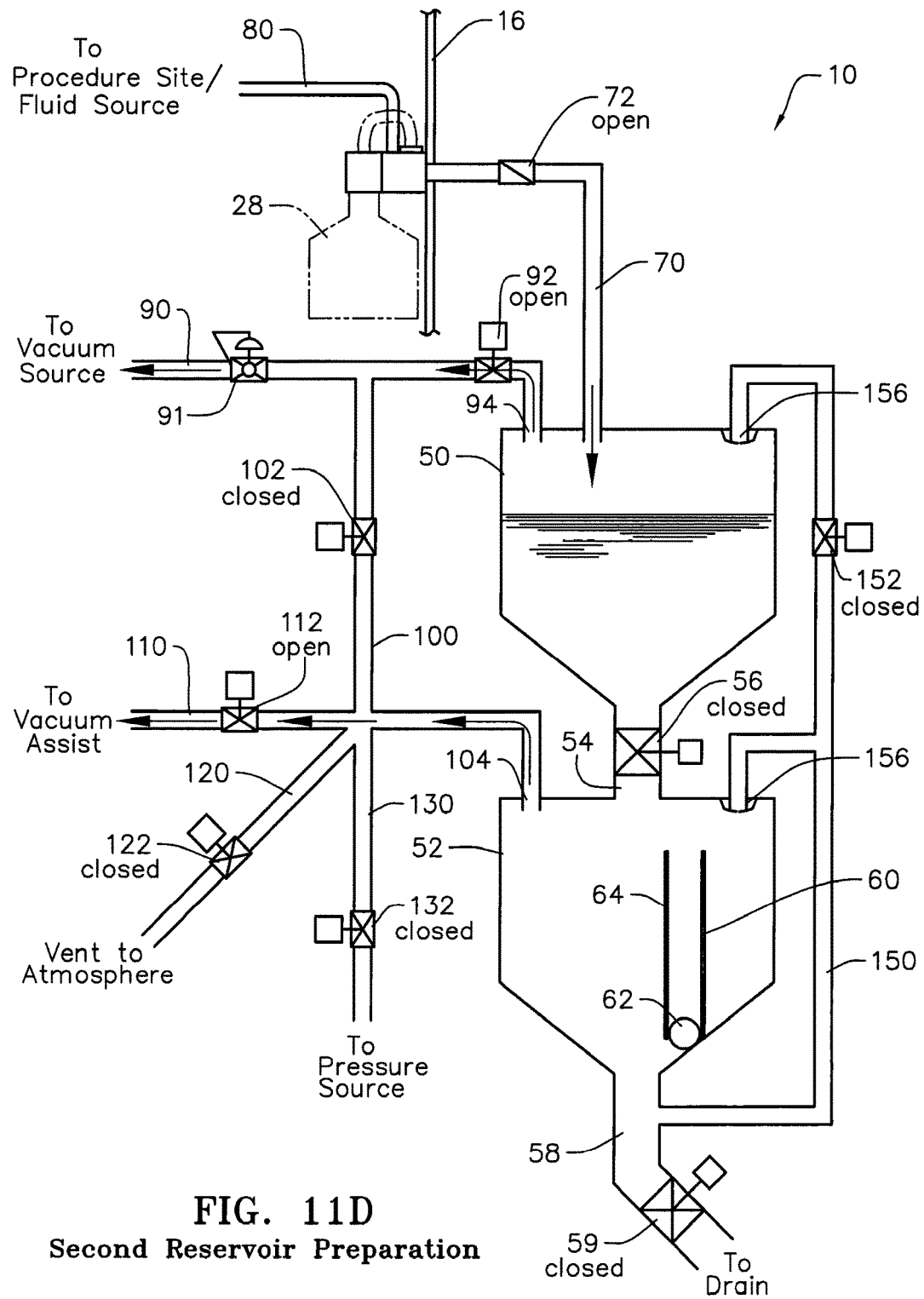

When the fluid in the second reservoir 52 has been evacuated (e.g., by the ball float 62 within the sensor tube 64 dropping to trigger a switch at the bottom of the sensor tube 64 indicating that the fluid has been evacuated), a signal is generated which begins the "Second Reservoir Preparation" phase as depicted in FIG. 11D. The generated signal causes the PLC to close the valve of the fluid discharge mechanism 59 and to close the pressure line valve 132, and to subsequently cause the vacuum assist line valve 112 to open. With the vacuum assist line valve 112 open, the vacuum assist source draws air out of the second reservoir 52 until the negative pressure in the second reservoir is substantially equal to the negative pressure in the first reservoir in communication with the vacuum source. Upon the equalization of the negative pressures in the first and second reservoirs (which may be detected by a pressure transducer or other suitable sensor), a signal is generated to cause the PLC to open the auxiliary line valve 102 and the fluid transfer valve 56 to permit the fluid that has been collecting in the first reservoir 50 to flow into the second reservoir 52 thereby repeating the process beginning with the "Fluid In" phase as depicted in FIG. 11A, except that the vacuum line valve 92 remains open until the procedure is completed and Stop Suction 212 is selected on the touch pad. It should be appreciated that it is desirable to equalize the negative pressure in the first and second reservoirs prior to opening the fluid transfer valve 56 to avoid or minimize a sudden drop or change in negative pressure in the first reservoir 50 (which could result in inconsistent suction through the suction hose 80 at the procedure site) which may occur if there is a significant pressure differential between the first and second reservoirs.

The "Fluid In", "Relief and Measure", "Drain" and "Second Reservoir Preparation" phases as depicted in FIGS. 11A-11D are repeated as necessary until the medical procedure is completed.

The fluid collection and disposal process of the embodiment of FIG. 6 is substantially similar to that of the embodiment of FIG. 5, except that because the vacuum assist has been eliminated in the embodiment of FIG. 6, after the fluid is drained from the second reservoir 52, the "Second Reservoir Preparation" phase is performed by the PLC generating a signal to open the auxiliary line valve 102 to equalize the negative pressure in the second reservoir 52 with the negative pressure in the first reservoir 50 before the fluid transfer valve 56 is opened to begin repeating the "Fluid In" phase.

Similarly, the fluid collection and disposal process of the embodiment of FIG. 7 is substantially similar to that of the embodiment of FIG. 6, except that because the vacuum assist and the pressure source have been eliminated in the embodiment of FIG. 7, the fluid is drained from the second reservoir 52 during the "Drain" phase via gravity alone and therefore the vent line valve 122 remains open until the fluid is drained from the second reservoir. When the fluid is drained from the second reservoir 52, the PLC generates a signal to close the vent line valve 122 and to initiate the "Second Reservoir Preparation" phase by opening the auxiliary line valve 102 to equalize the negative pressure in the second reservoir 52 with the negative pressure in the first reservoir 50 before the fluid transfer valve 56 is opened to begin repeating the "Fluid In" phase.

The fluid collection and disposal process of the embodiment of FIG. 8 is the same as described in connection with FIGS. 11A-11D, but the Cleaning Cycle Process will vary as described later.

The fluid collection and disposal process of the embodiment of FIG. 10 is substantially the same as that described in connection with the embodiment of FIG. 5 except that rather than utilizing a ball float type volume sensor, the embodiment of FIG. 10 shows the fluid sensor 60 as being a flow meter rather than a float-type sensor.

Fluid in Phase—FIG. 9 Embodiment

Figure 12A:
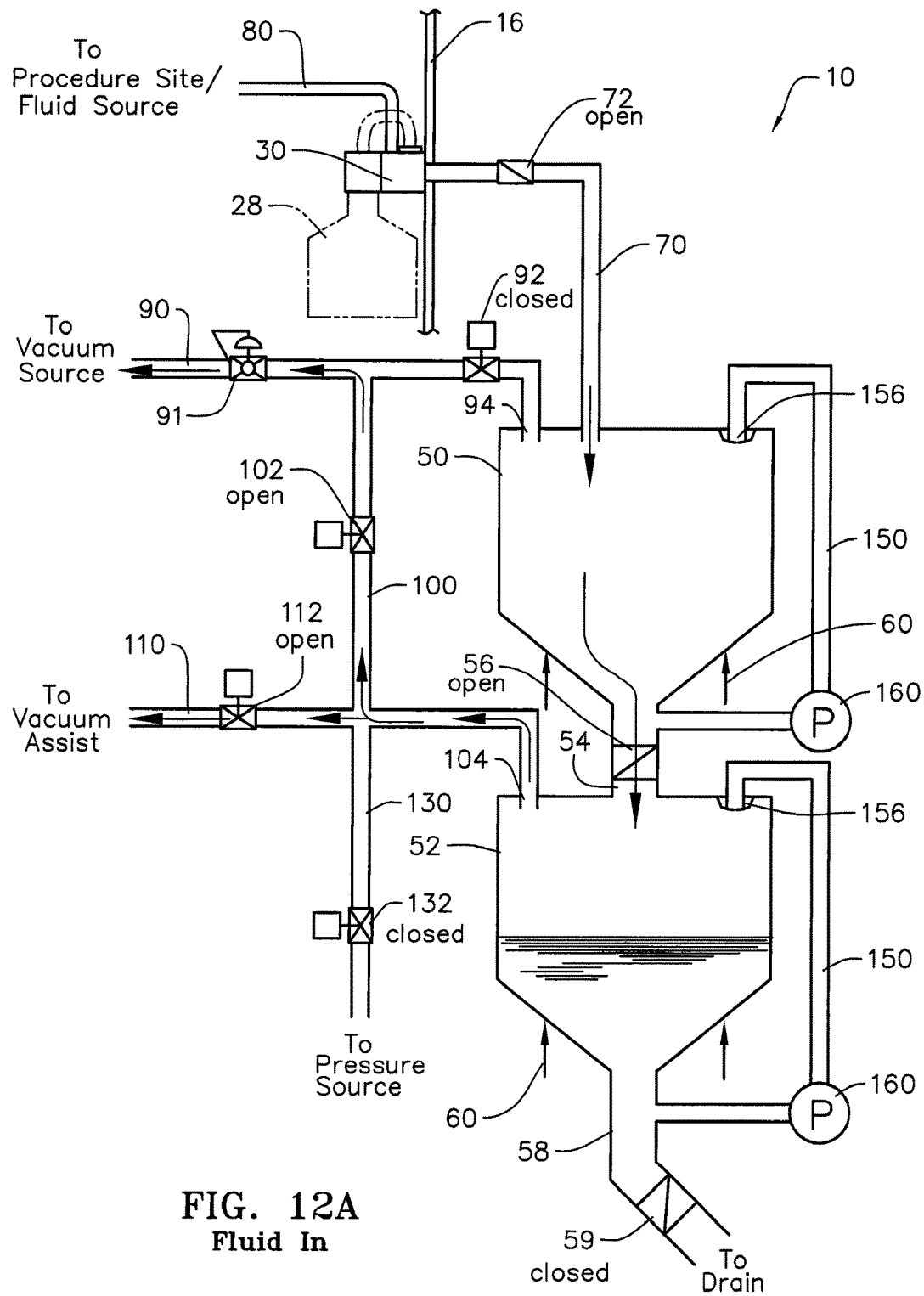
FIGS. 12A-12D schematically illustrate the fluid waste collection and disposal system of FIG. 9 showing various steps of using the system to collect and dispose of fluid waste.

Reference to FIGS. 12A-12D are made to describe the fluid collection and disposal process for the embodiment of FIG. 9. Referring to FIG. 12A, upon selecting the Start Suction operation 210, the initial "Fluid In" phase is initiated by the PLC generating a signal to open the auxiliary line valve 102 and/or the vacuum assist line valve 112 permitting communication of the vacuum source and/or vacuum assist source with the second reservoir 52 (as indicated by the arrows).

As previously identified, in the embodiment of FIG. 9, the fluid transfer valve 56 and fluid discharge mechanism 59 comprise check valves which are not electronically controllable by the PLC. Because the fluid transfer check valve 56 is biased in the normally closed position, the fluid transfer check valve 56 will remain closed until the negative pressure in the second reservoir sufficiently exceeds the negative pressure in the first reservoir to overcome the bias forcing the fluid transfer check valve 56 to open. During the initial Fluid In phase, the vacuum line valve 92 remains closed and thus, the first reservoir is not in communication with the vacuum source. As a result, the fluid transfer check valve 56 is forced to open when the auxiliary line valve 102 and/or vacuum assist line valve 112 are opened because only the second reservoir is in communication with the vacuum source and/or vacuum assist source.

With the fluid transfer check valve 56 open, the first reservoir is now in communication with the vacuum source. The negative pressure inside the reservoirs 50, 52 creates suction through the inlet line 70, which overcomes the bias of the normally closed inlet line check valve 72, such that suction is provided to the suction ports 304 of the manifold 30.

The operator attaches the suction hose 80 to the suction ports 304. If a filter is used, the filter is connected to the suction ports 304 and the suction hoses are connected to inlets on the filter. The distal end of the suction hose 80 includes an end effector (not shown) which typically includes a regulator for controlling the amount of suction through the end effector. The operator may also adjust the amount of Table Suction 204 using the vacuum adjust controller(s) 24. When the end effector on the suction hose 80 is placed in contact with fluid, fluid is drawn through the suction hose 80 and into the first reservoir 50 and then into the second reservoir 52 due to the fluid transfer valve 56 being open. The fluid entering the first and/or second reservoirs 50, 52 is preferably visible through the window 22 in the front panel. As noted earlier, a light strip may be used to back-light the aspirated fluid entering in the reservoirs so it can be better viewed by the operator.

Relief and Measure Phase—FIG. 9 Embodiment

Figure 12B:
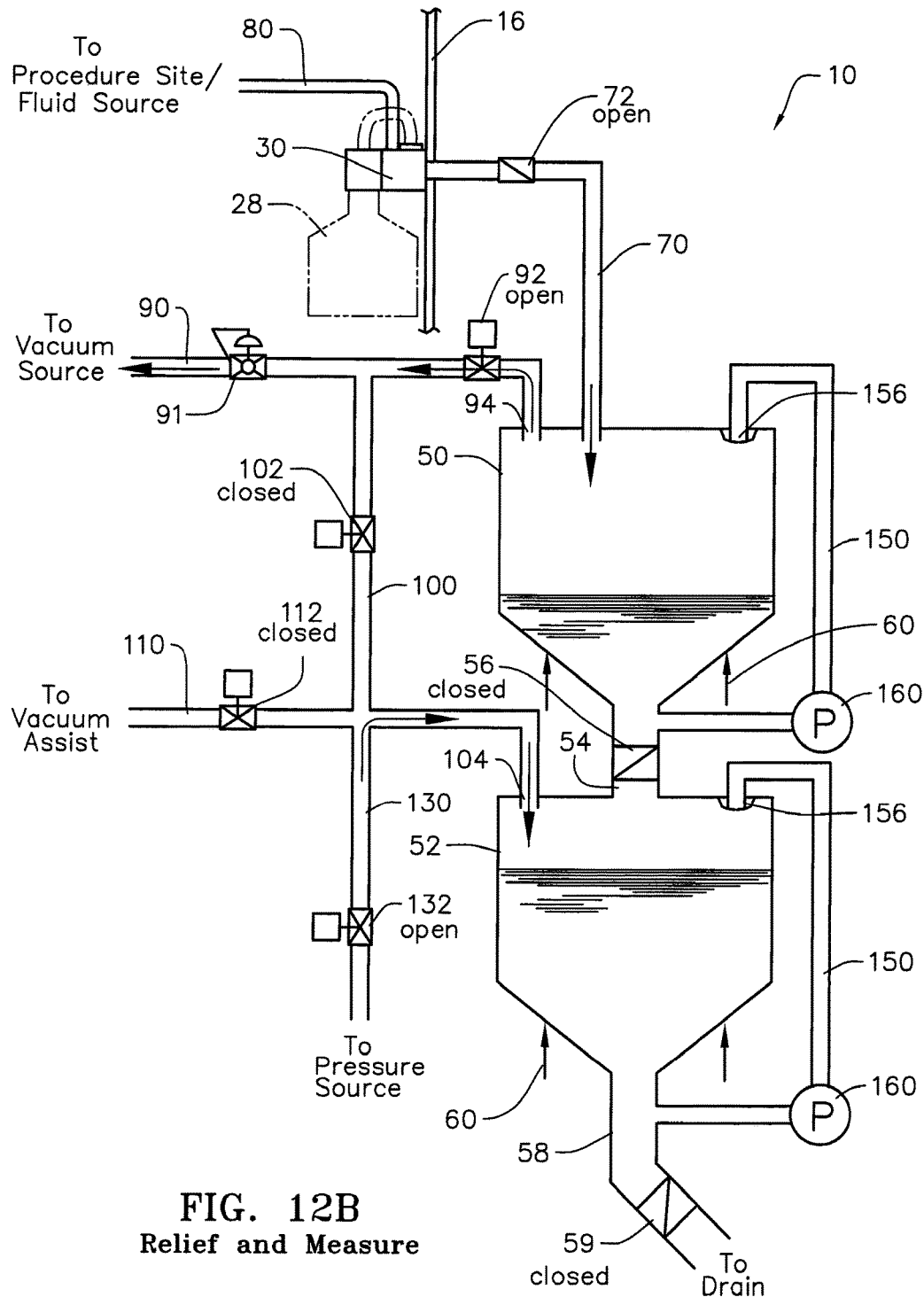

When the fluid in the second reservoir 52 reaches a predetermined volume or fill level (as detected by the load cell fluid sensor 60), a signal is generated which begins the "Relief and Measure" phase as illustrated in FIG. 12B. The generated signal causes the PLC to open the vacuum line valve 92. After the vacuum line valve 92 is opened, the PLC generates a signal to close the auxiliary line valve 102 and/or vacuum assist line valve 112 (depending on if both are provided and both are open) to isolate the second reservoir 52 from the vacuum source and/or vacuum assist source. With the second reservoir 52 isolated from the vacuum source, the fluid transfer check valve 56 will return to its normally closed position due to the lack of greater negative pressure in the second reservoir sufficient to overcome the check valve bias, thereby isolating the second reservoir 52 from the first reservoir 50. It should be appreciated that the first reservoir remains under negative pressure via the open vacuum line valve 92, such that communication of the vacuum source with the first reservoir is not interrupted. When the fluid transfer valve 56 and auxiliary line valve 102 are closed, a signal is generated to cause the pressure line valve 132 to momentarily open to relieve the negative pressure in the second reservoir 52 until it is brought to atmosphere. The mass/weight and/or volume of fluid in the second reservoir 52 is then determined or otherwise measured and recorded by the fluid measuring system 400 as described later.

Drain Phase—FIG. 9 Embodiment

Figure 12C:
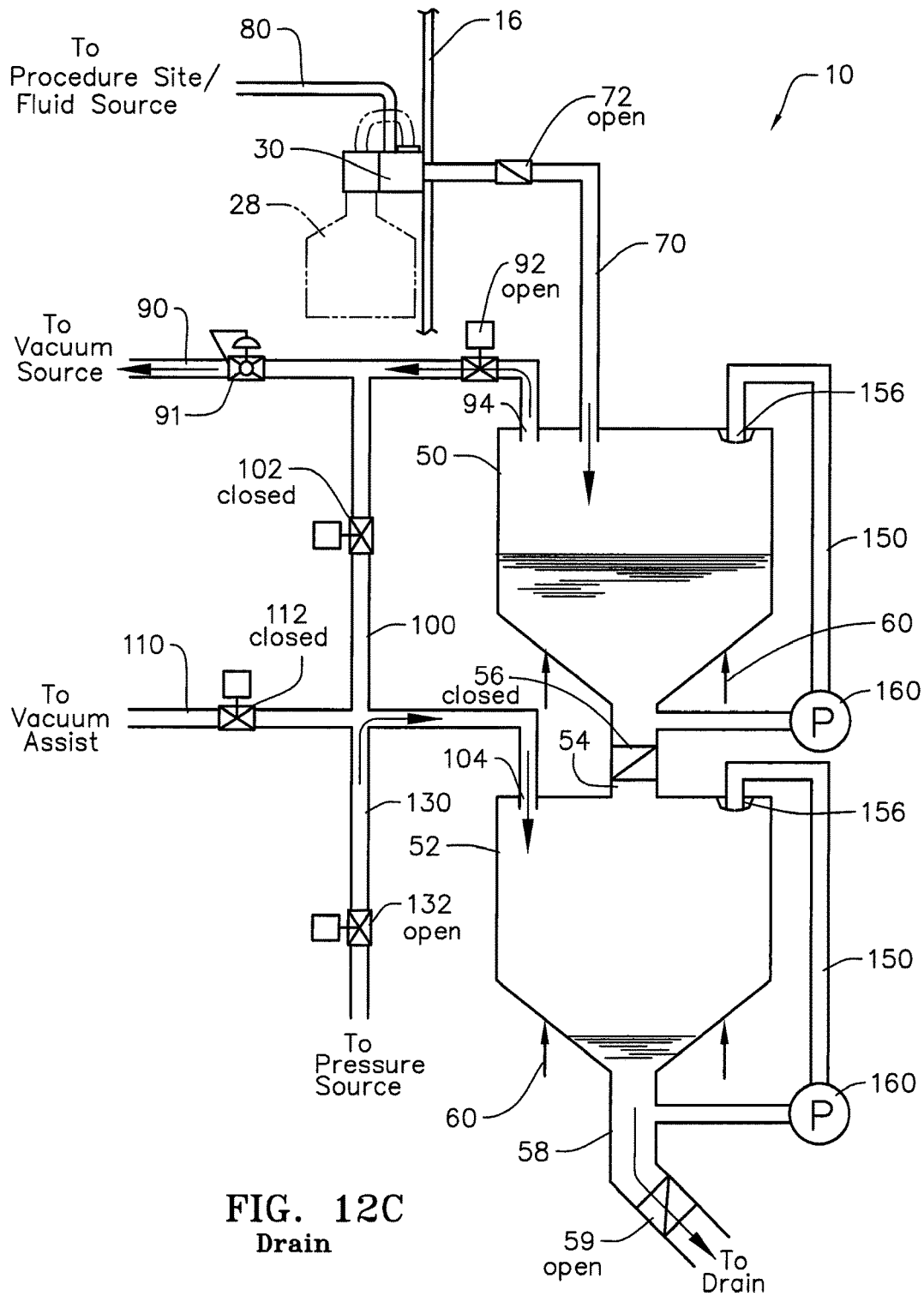

Once the mass and/or volume of the fluid in the second reservoir has been determined and recorded, the "Drain" phase as illustrated in FIG. 12C is initiated by the PLC generating a signal to cause the pressure line valve 132 to open to pressurize the second reservoir 52 sufficient to overcome the bias on the normally closed check valve of the fluid discharge mechanism 59 causing it to open and forcefully evacuate the fluid from the second reservoir 52.

Second Reservoir Preparation Phase—FIG. 9 Embodiment

Figure 12D:
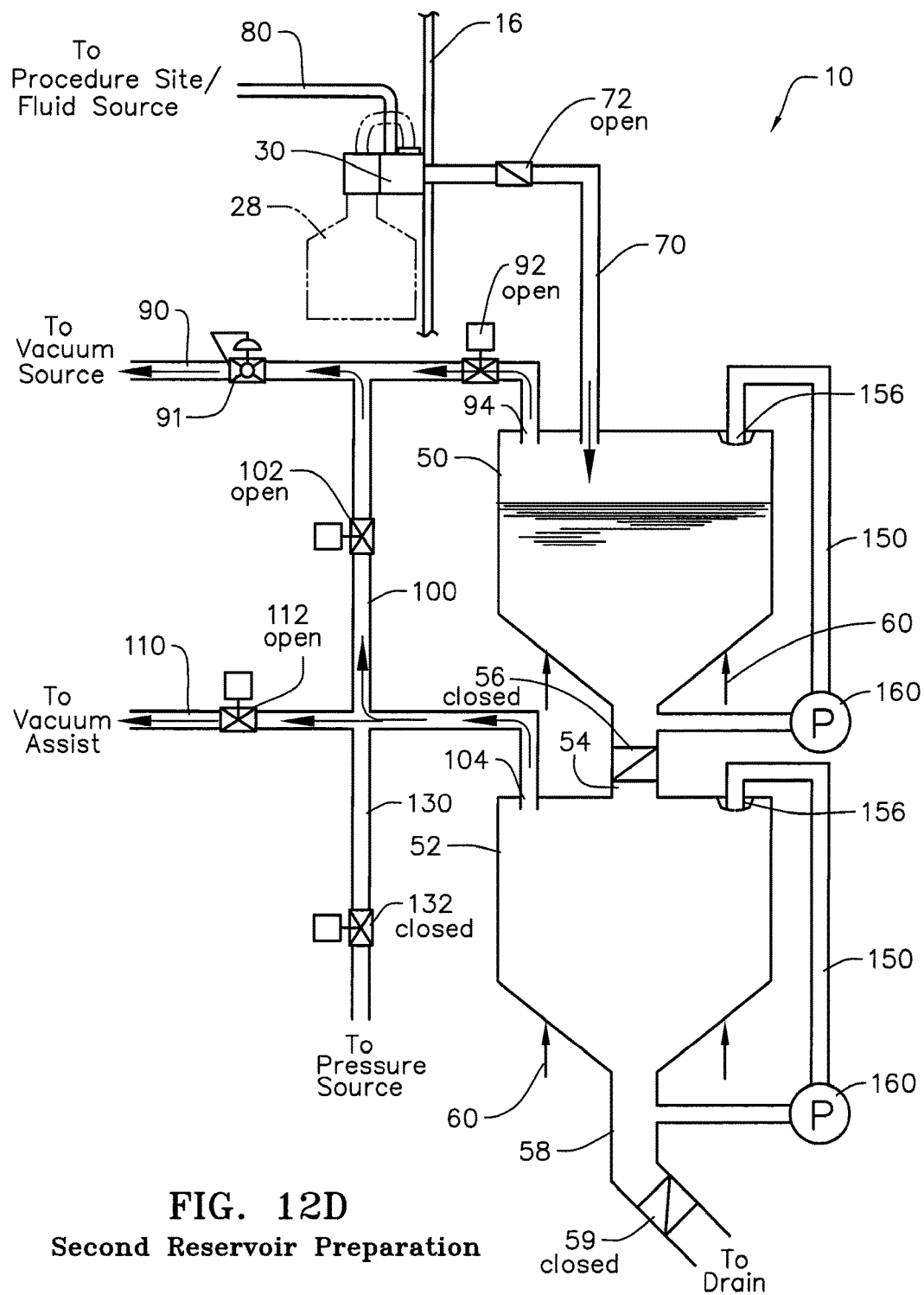

When the fluid in the second reservoir 52 has been evacuated (e.g., as detected by the load cell), the "Second Reservoir Preparation" phase is initiated as depicted in FIG. 12D by the PLC generating a signal to cause the pressure line valve 132 to close, and to cause the auxiliary line valve 102 and/or vacuum assist line valve 112 to open to equalize the negative pressure in the second reservoir with the negative pressure of the first reservoir. As the negative pressure in the second reservoir decreases, the check valve of the fluid discharge mechanism 59 returns to its normally closed position. The negative pressure in the second reservoir is increased (or the negative pressure in the first reservoir is caused to slightly bleed off via the PLC generating a signal to cause the regulator 91 to open thereby reducing the negative pressure in the first reservoir) until there is a slight pressure differential between the second reservoir and first reservoir sufficient to overcome the bias of the fluid transfer check valve 56 causing it to open, permitting the fluid being collected in the first reservoir to again flow into the second reservoir 52 thereby repeating the "Fluid In" phase as depicted in FIG. 12A, except that the vacuum line valve 92 remains open until the procedure is completed and Stop Suction 212 is selected on the touch pad. The "Fluid In", "Relief and Measure", "Drain" and "Second Reservoir Preparation" phases as depicted in FIGS. 12A-12D are repeated as necessary until the medical procedure is completed.

It should also be appreciated that in each of the embodiments of FIGS. 5-10, the volume of the first reservoir 50 has sufficient capacity so that it does not fill faster than is required to complete the "Relief and Measure", "Drain" and "Second Reservoir Preparation" phases. A fluid sensor may be disposed to monitor the fluid level, volume or mass in the first reservoir 50 similar to the fluid sensor 60 for monitoring the second reservoir to generate signals to trigger different phases of the fluid collection and disposal process and/or to trigger an emergency shut-off of the vacuum line valve 92 if fluid in the first reservoir 50 reaches a predetermined level to prevent fluid from being drawn into the main vacuum line 90 in the event of a malfunction.

It should be appreciated that, with each embodiment, because fluid continues to be drawn into the first reservoir 50 without interruption while the fluid in the second reservoir 52 is being measured and drained, the system 10 has an unlimited capacity and the suction through the suction hoses 80 remains continuous and substantially constant such that there is no interruption to the medical procedure.

Upon completion of the medical procedure, the operator selects the "Stop Suction" operation 212 using the touch screen 20 thereby causing the vacuum line valve 92 (and the vacuum assist line valve 112 in the FIG. 5A and FIG. 6 embodiments) to actuate and close-off the vacuum source from both reservoirs 50, 52.

Fluid Measuring System

A fluid measuring system 400 is provided to determine, record and display the amount of waste fluid collected during the medical procedure. It is desirable for the surgical team to know the volume of fluid loss from the patient during the procedure by comparing the volume of the collected fluid in relation to the known quantities of saline or other fluids introduced into the patient during the procedure so as to ensure that no excess fluid remains within the body cavity and to ensure that excessive blood loss has not occurred; both being conditions that may place the patient at an increased post-operative risk.

The fluid measuring system 400 may comprise appropriate programming of the PLC to simply add the known liquid volume of the second reservoir 52 (e.g., based on the point at which the ball float triggers the switch as in the embodiments of FIGS. 5-7 or at the position of the electronic sensor as shown in the embodiment of FIG. 8) to the previously recorded value stored in memory from the previous cycle(s).

Alternatively, if a load cell is used for the fluid volume sensor 60, as illustrated in the embodiment of FIG. 9, the volume may be determined by programming the PLC to calculate the volume based on the mass/weight detected by the load cell multiplied by the specific gravity of the fluid being collected (within an acceptable range) and adding this value to the previously recorded values stored in memory from the previous cycles. If a load cell is used, the fluid volume may be determined while the second reservoir 52 remains under negative pressure so the step of determining the volume could be performed prior to the venting/relief step described above. The running total of collected fluid volume is preferably caused to be displayed on the Fluid Collected indicator 200 of the display 20. Alternatively, a volume measuring pump or other suitable system may be used to measuring and record the fluid within the second reservoir or as the fluid is being drained or evacuated during the "Drain" phase or while the fluid passes through the fluid inlet line 70 as illustrated in FIG. 10.

Cleaning Cycle Process

Upon pressing the Stop Suction operation after the procedure is completed, the operator may be prompted on the touch screen display 20 to select the "Start Clean Cycle" operation 214. Upon pressing the Start Clean Cycle operation, the operator may be instructed on the screen display 20 to remove the suction hose(s) 80 (and/or filter if used) from the suction port(s) 304 and to attach the cleaning solution bottle 28 to the cleaning solution hanger assembly 310. It should be appreciated that the cleaning solution bottle 28 may be attached to the block 314 and the cleaning solution tubes 324 already attached to the nipples 322, 326 as previously described before the medical procedure begins. In which case, the screen display 20 may instruct the operator to invert the bottle 28 as illustrated in FIG. 3B. Rather than utilizing bottles or bags, a refillable cleaning solution reservoir may be provided internal or external to the housing 12. The cleaning solution may be any solution suitable for cleaning and/or disinfecting bodily fluids that come into contact with the internal surface areas of the system 10.

The Cleaning Cycle Process of the system 10 is described below with reference to FIGS. 13A-13E which correspond to the embodiment of FIG. 5. A brief description of the cleaning process for the embodiments of FIGS. 6-8 and 10 follow the description of the embodiment of FIG. 5. A more detailed discussion of the cleaning processes is provided for the embodiment of FIG. 9 with reference to FIGS. 14A-14F in view of the structural and functional difference of the embodiment of FIG. 9 as compared to the other embodiments.

Cleaning Solution in Phase—FIG. 5 Embodiment

Figure 13A:
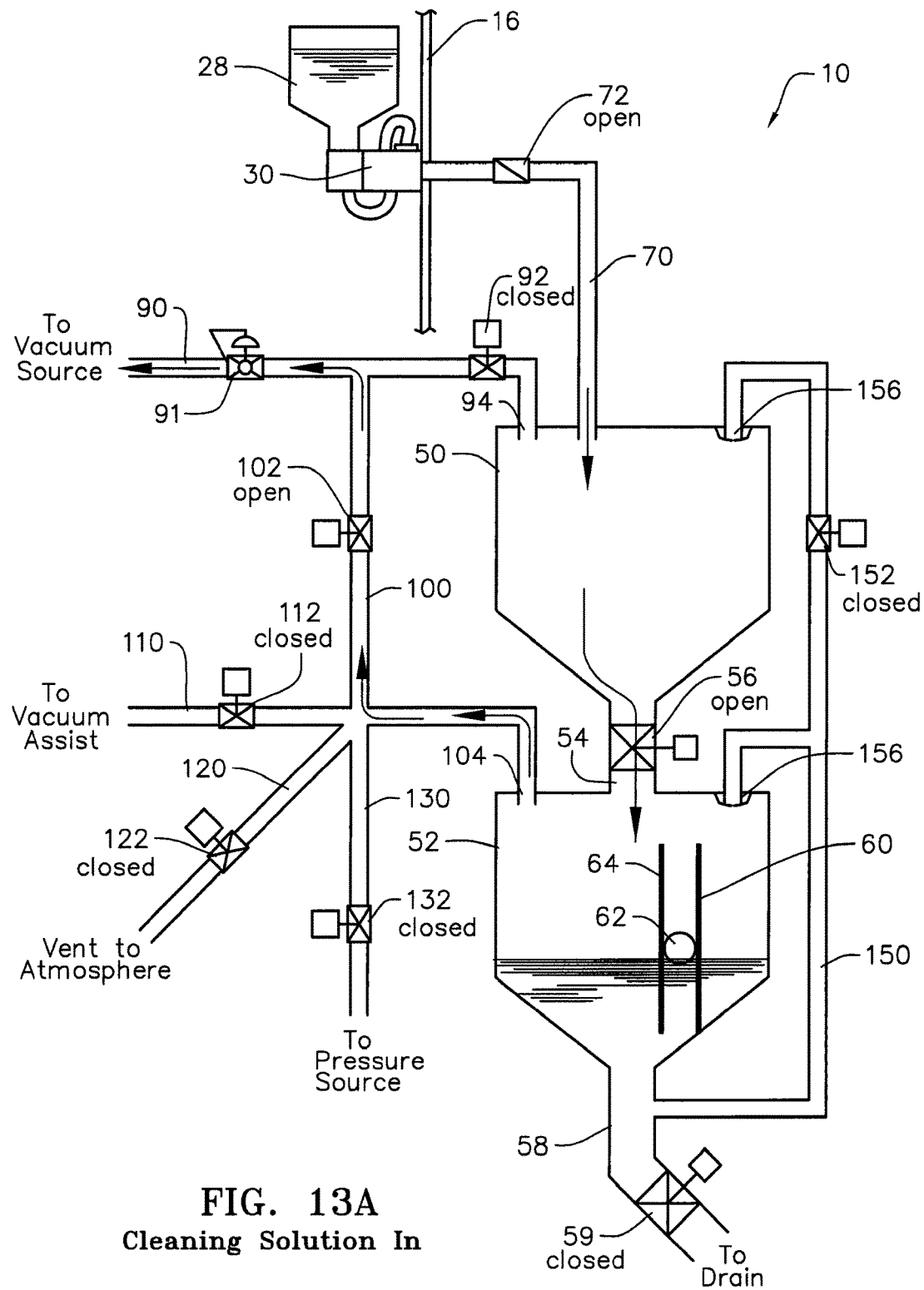
FIGS. 13A-13E schematically illustrate the fluid waste collection and disposal system of FIG. 5 showing various steps a process for cleaning the system.

When the Start Clean Cycle is initiated (whether by pressing the Start Clean Cycle operation on the touch screen 20 or by triggering a switch upon inverting the bottle 28 as previously mentioned), the "Cleaning Solution In" phase begins as depicted in FIG. 13A, by generating a signal to open the electronically controllable fluid transfer valve 56 and auxiliary line valve 102 permitting communication of the vacuum source with the second reservoir 52, and to the first reservoir 50 through the open fluid transfer valve 56 (all other valves are closed). Because the fluid transfer valve 56 is in the open position, it should be appreciated that the first and second reservoirs 50, 52 will have substantially the same negative pressure due to the air being evacuated (as indicated by the arrows) by the vacuum source. The negative pressure inside the reservoirs 50, 52 creates suction through the inlet line 70, which overcomes the bias of the normally closed inlet line check valve 72, such that the cleaning solution is drawn into the first reservoir 50, which then flows into the second reservoir through the open fluid transfer valve 56.

Cleaning Solution Recirculation Phase—FIG. 5 Embodiment

Figure 13B:
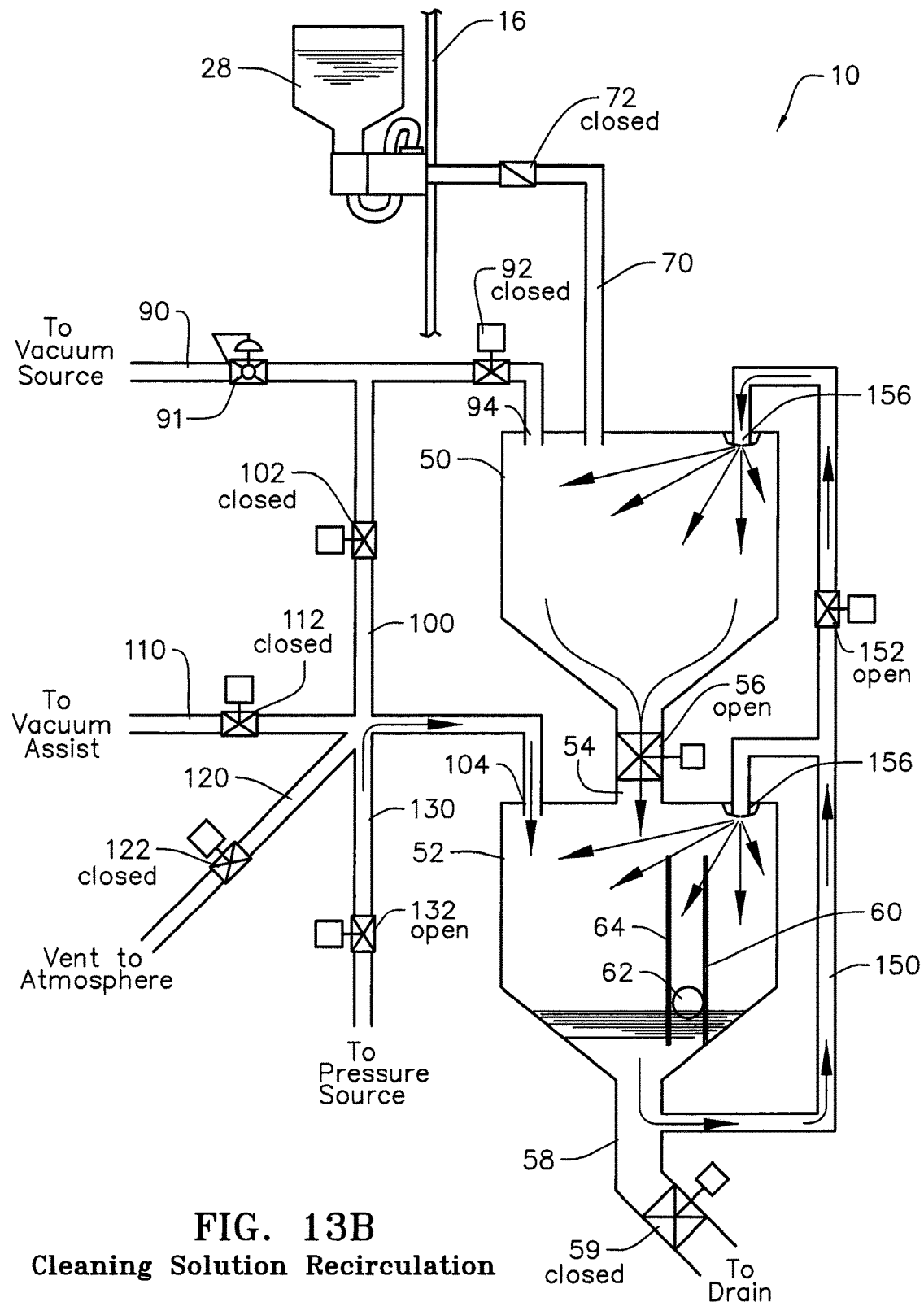

When a predetermined amount of cleaning solution is drawn into the reservoirs 50, 52 (e.g., ⅓ to ½ of the volume of the cleaning solution bottle), the "Cleaning Solution Recirculation" phase as depicted in FIG. 13B is initiated by the PLC generating a signal to cause the auxiliary line valve 102 to close and to cause the recirculation line valve 152 and the pressure line valve 132 to open. Once the vacuum source is shut off from the reservoirs 50, 52, the inlet line check valve 72 automatically closes. The predetermined amount of cleaning solution entering the reservoirs 50, 52 may be based on the fluid sensor 60 or a timer or other suitable measuring mechanism. The pressure from the pressure source forces the cleaning solution through the recirculation line 150 which splits toward each reservoir 50, 52 terminating in nozzles 156. The nozzles 156 direct the cleaning solution to forcefully spray the sidewalls of the reservoirs 50, 52.

Relief Phase—FIG. 5 Embodiment

Figure 13C:
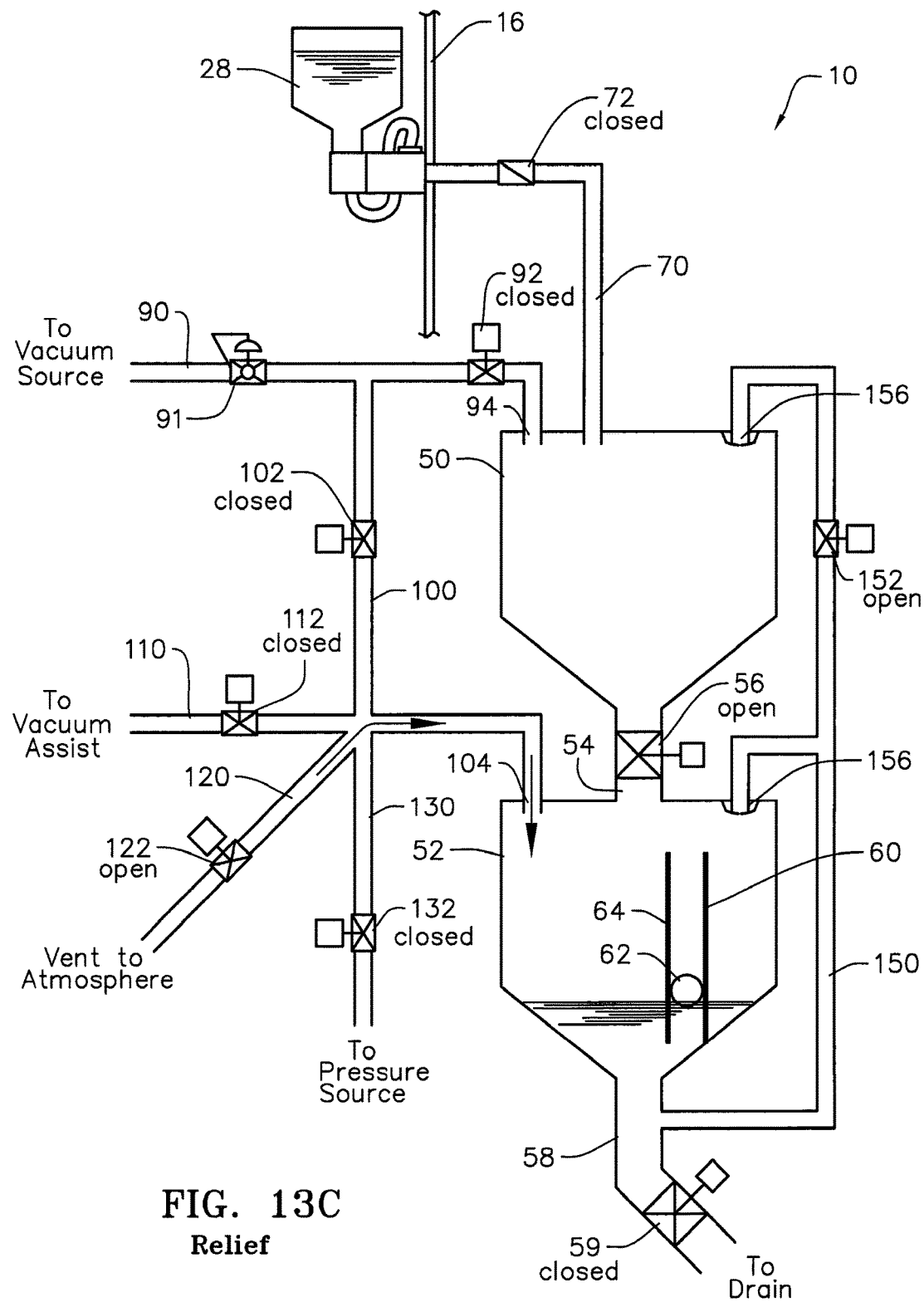

After a predetermined time period, or when a pressure equilibrium is reached, the "Relief" phase as depicted in FIG. 13C is initiated by the PLC generating a signal to close the pressure line valve 132 and to open the vent line valve 122 to release the pressure in the reservoirs 50, 52.

Repeat Recirculation Phase—FIG. 5 Embodiment

Figure 13D:
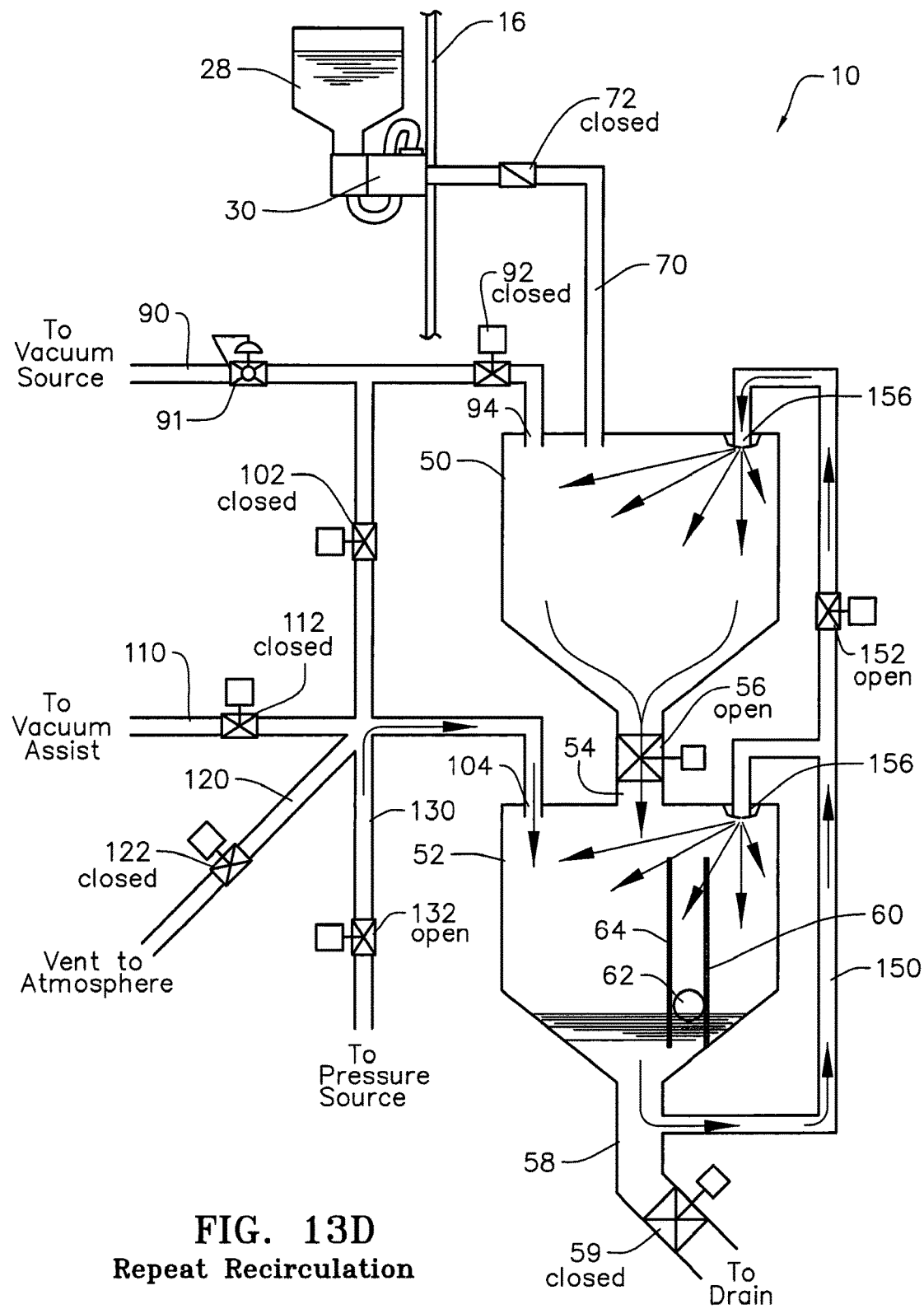

After relieving the pressure in the reservoirs, the "Repeat Recirculation" phase as depicted in FIG. 13D is initiated to recirculate the initial volume of cleaning solution, by the PLC generating a signal to close the vent line valve 122 and open the pressure line valve 132 to again force the cleaning solution through the recirculation lines 150 and through the nozzles 156. The "Relief" phase and "Repeat Recirculation" phase may be repeated several times.

Drain Cleaning Solution Phase—FIG. 5 Embodiment

Figure 13E:
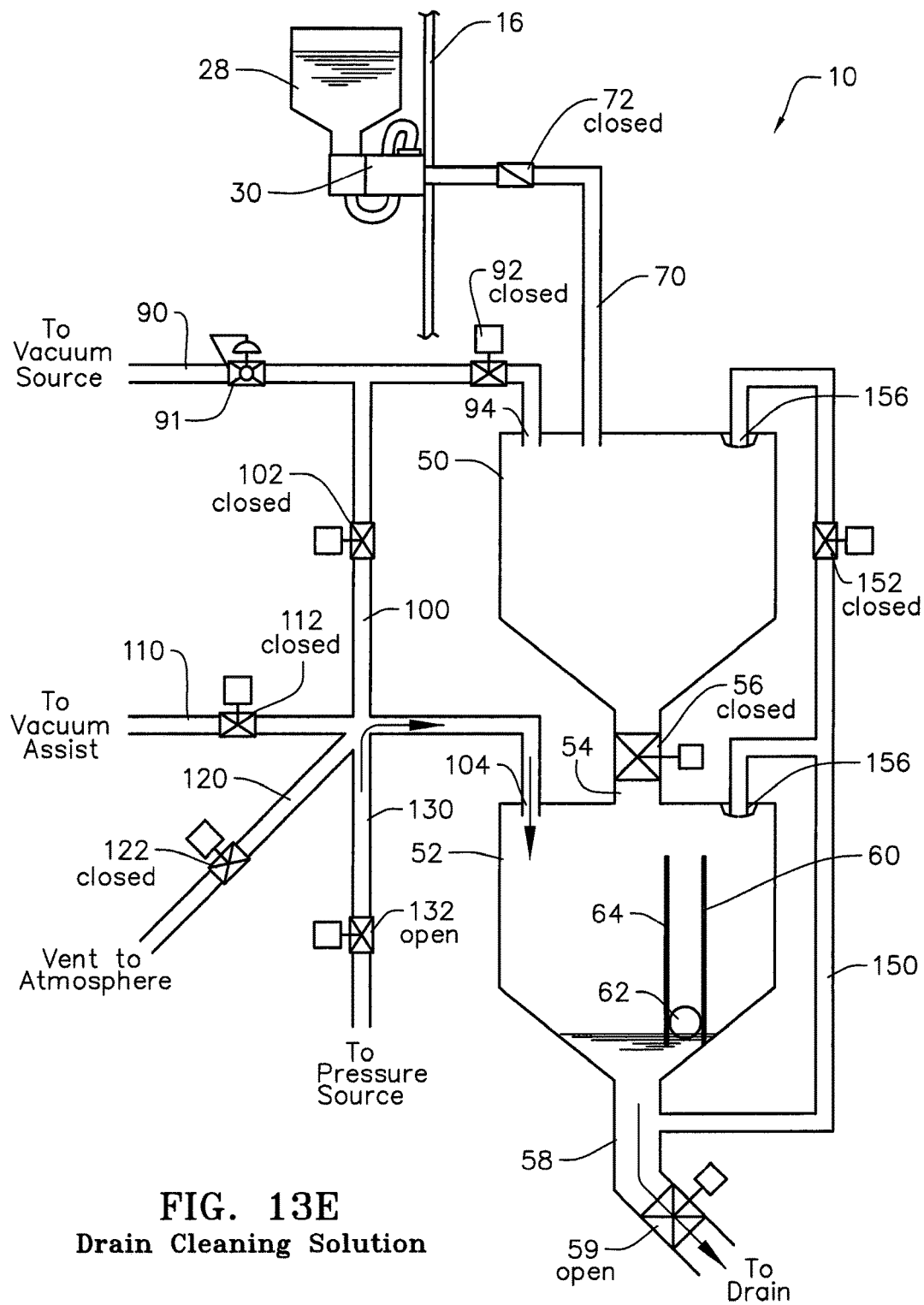

After two or more recirculations of the initial volume of cleaning solution, the "Drain Cleaning Solution" phase as depicted in FIG. 13E is initiated by the PLC generating a signal to close the vent line valve 122 and to open the drain valve 59 and pressure line valve 132 to evacuate the cleaning solution from the second reservoir. After the initial volume of cleaning solution is drained, the "Cleaning Solution In", "Cleaning Solution Recirculation", "Relief", "Repeat Recirculation" and "Drain Cleaning Solution" phases are repeated until the cleaning solution bottle 28 is emptied and/or until the reservoirs are adequately cleaned. Additional or alternative valving, piping and sequencing may be desirable to facilitate thorough cleaning of the reservoirs and components.

In the embodiment of FIG. 7 in which the pressure source is eliminated, a vacuum powered cleaning cycle may be used whereby, instead of using the pressure source to force the cleaning solution through the recirculation lines 150, a signal may be generated to cause the vacuum line valve 92 and auxiliary line valve 102 to open which will draw the cleaning solution through the recirculation lines 150 and nozzles 156 to spray the reservoir sidewalls.

In the embodiment of FIG. 8 in which the a recirculation pump 160 is used in place of the recirculation line valve 152, the process will be substantially the same as described above in connection with the embodiment of FIG. 5, except that instead of generating a signal to open the recirculation line valve and the pressure line valve 132 to force the cleaning solution through the recirculation lines 150, a signal is generated to initiate the recirculation pump 160 during the respective phases to pump the cleaning solution through the recirculation lines 150.

Cleaning Solution into Second Reservoir Phase—FIG. 9 Embodiment

Reference to FIGS. 14A-14F are made to describe the Cleaning Cycle Process for the embodiment of FIG. 9. As previously identified, in the embodiment of FIG. 9, the fluid transfer valve 56 and fluid discharge mechanism 59 comprise check valves which are not electronically controllable by the PLC.

Figure 14A:
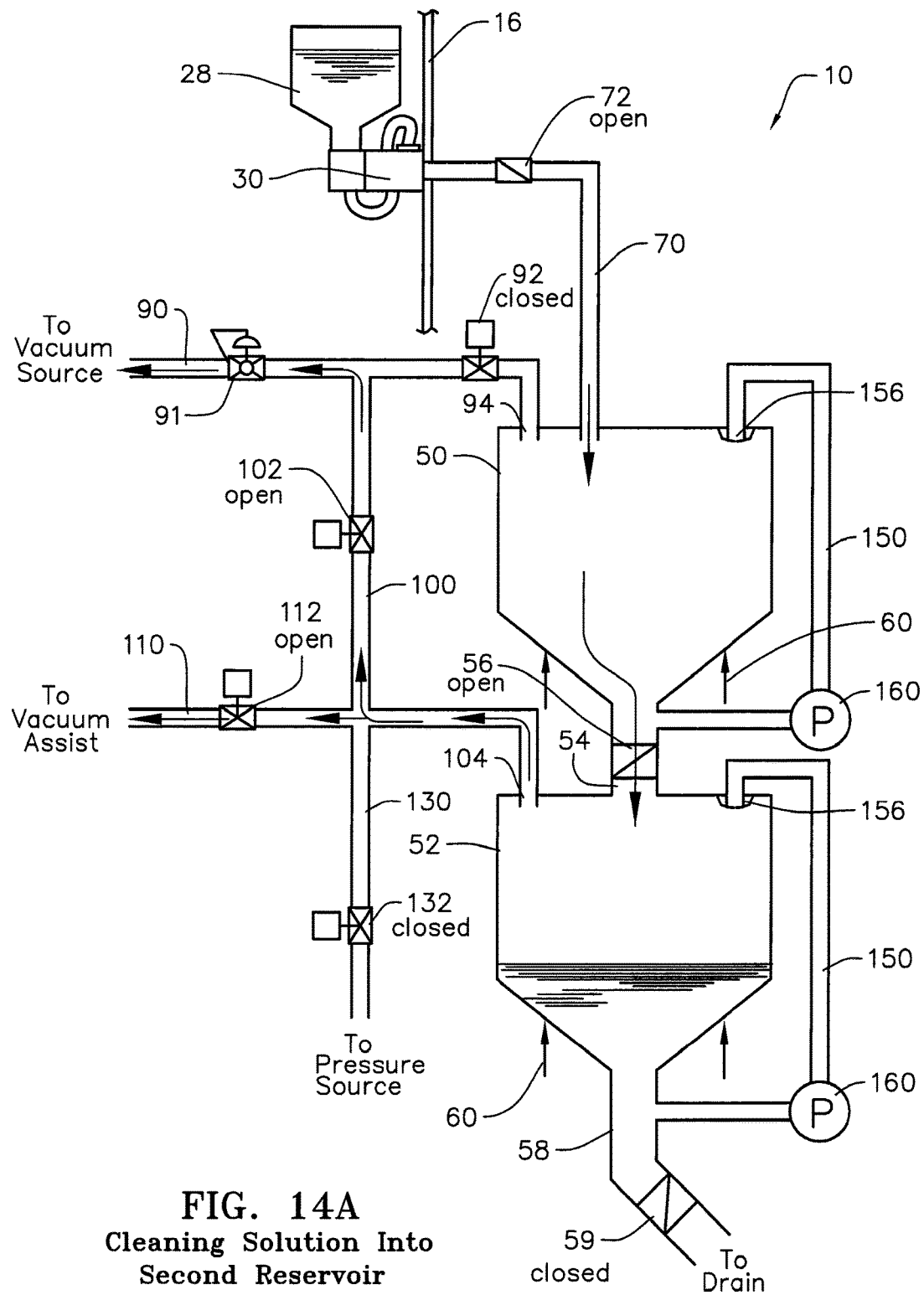
FIGS. 14A-14F schematically illustrate the fluid waste collection and disposal system of FIG. 9 showing various steps of a process for cleaning the system.

When the Start Clean Cycle is initiated (whether by pressing the Start Clean Cycle operation on the touch screen 20 or by triggering a switch upon inverting the bottle 28 as previously mentioned), the "Cleaning Solution Into Second Reservoir" phase begins as depicted in FIG. 14A, by generating a signal to cause the auxiliary line valve 102 and/or the vacuum assist line valve 112 to open (all other valves, including the vacuum line valve 92, are closed). As previously described in connection with FIG. 12A, because the vacuum line valve 92 is closed, the bias of the fluid transfer check valve 56 is overcome and is forced to open because only the second reservoir is in communication with the vacuum source and/or vacuum assist source. With the fluid transfer check valve 56 open, the first reservoir is now in communication with the vacuum source and the negative pressure inside the reservoirs 50, 52 creates suction through the inlet line 70, which overcomes the bias of the normally closed inlet line check valve 72, permitting the cleaning solution to begin flowing into the first reservoir.

Cleaning Solution into First Reservoir Phase—FIG. 9 Embodiment

Figure 14B:
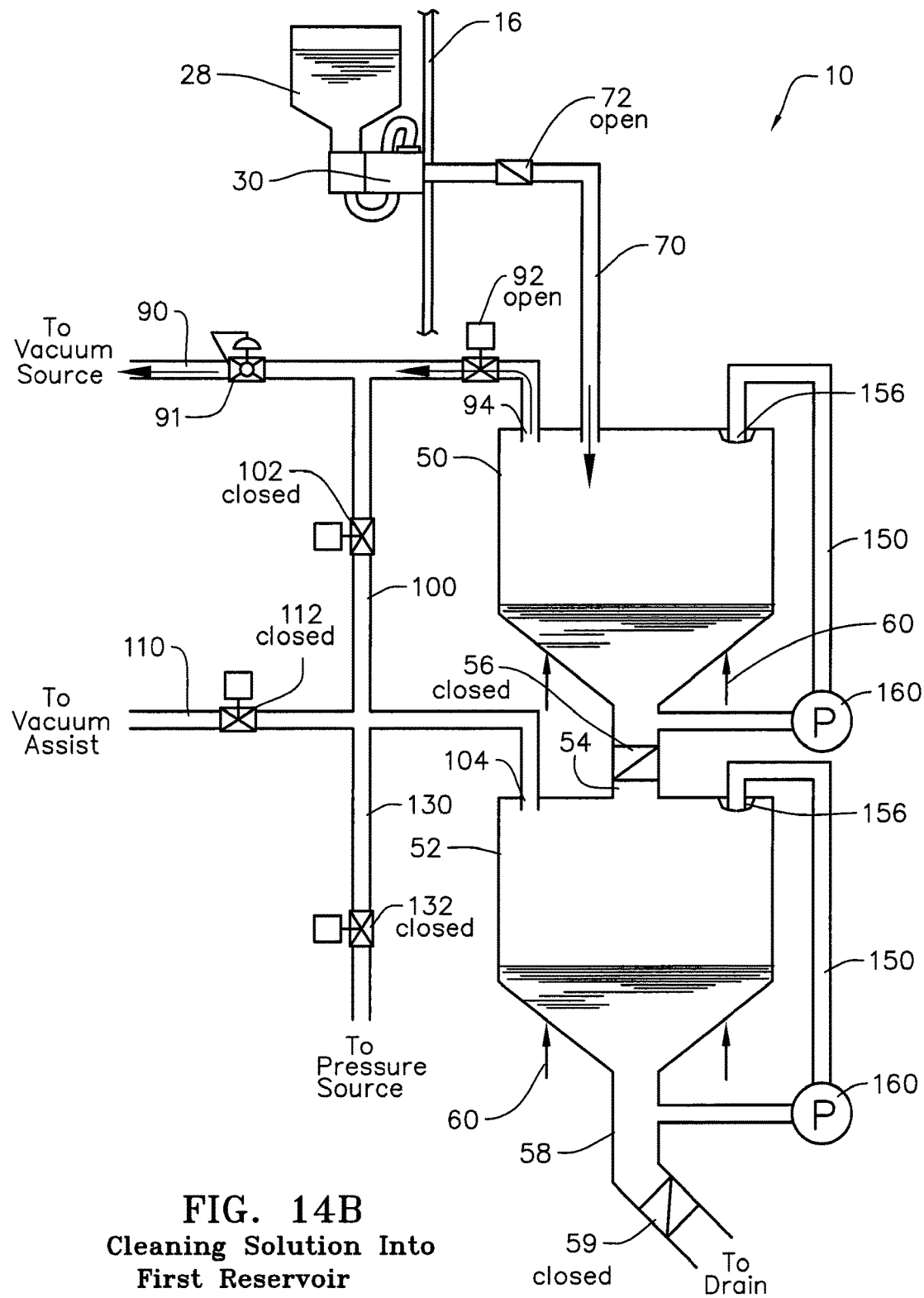

When a predetermined amount of cleaning solution is drawn into the second reservoir 52 (e.g., ¼ of the volume of the cleaning solution bottle) as detected by the fluid sensor 60 for the second reservoir (or based on time, or based on a flow meter or other means), the "Cleaning Solution into First Reservoir" phase as depicted in FIG. 14B is initiated by the PLC generating a signal to cause the auxiliary line valve 102 (and the vacuum assist line valve 112, if provided and open) to close. Once the vacuum source is shut off from the second reservoir 52, the fluid transfer check valve 56 closes. The PLC then generates a signal to cause the vacuum line valve 92 to open which causes a predetermined amount of cleaning solution to be drawn into the first reservoir 50 (e.g., ¼ of the volume of the cleaning solution bottle) as detected by the fluid sensor 60 for the first reservoir (or based on time, or based on a flow meter or other means), at which point a signal is generated by the PLC to close the vacuum line valve 92, which causes the inlet line valve 72 to close, preventing any additional cleaning solution from entering the first reservoir 50.

Relief Phase—FIG. 9 Embodiment

Figure 14C:
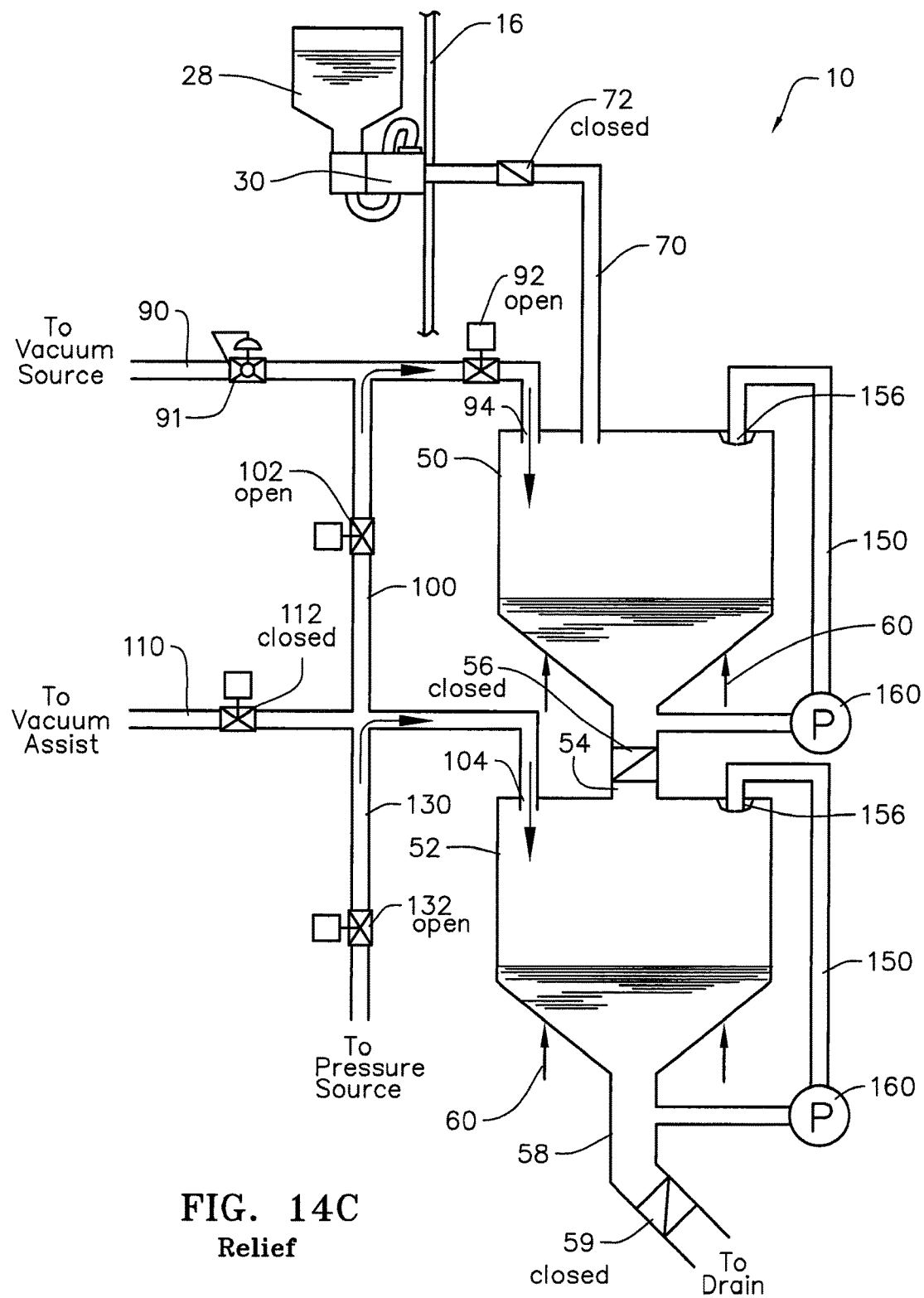

After both the first and second reservoirs have the predetermined amount of cleaning solution is drawn into the reservoirs 50, 52 (e.g., ⅓ to ½ of the volume of the cleaning solution bottle), the "Relief" phase as depicted in FIG. 14C is initiated by the PLC generating a signal to close the regulator 91 and to open the pressure line valve 132, the auxiliary line valve 102 and the vacuum line valve 92, permitting air to enter and relieve the negative pressure in both reservoirs 50, 52. Alternatively, rather than opening the auxiliary line valve, it may remain closed and the PLC may generate a signal to cause the regulator 91 to bleed to atmosphere and to opening the vacuum line valve thereby relieving the negative pressure in the first reservoir.

Cleaning Solution Recirculation Phase—FIG. 9 Embodiment

Figure 14D:
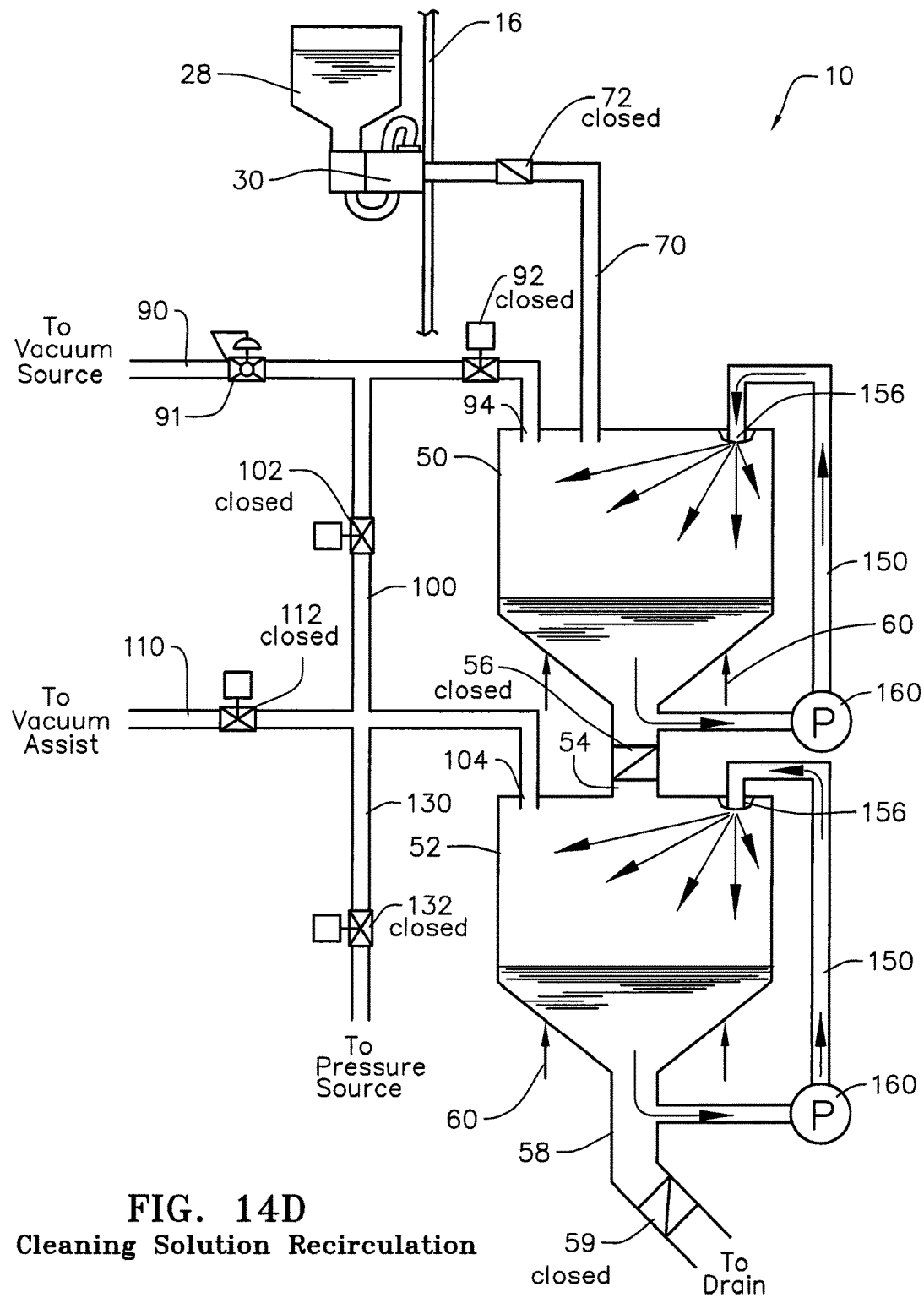

Once the reservoirs are brought to atmosphere, the "Cleaning Solution Recirculation" phase as depicted in FIG. 14D is initiated by the PLC generating a signal to actuate the recirculation pumps 160 which pumps the cleaning solution through the respective recirculation lines 150 and back into the respective reservoirs 50, 52 for a predetermined period of time. The nozzles 156 direct the cleaning solution to forcefully spray the sidewalls of the reservoirs 50, 52.

First Reservoir Drain Phase—FIG. 9 Embodiment

Figure 14E:
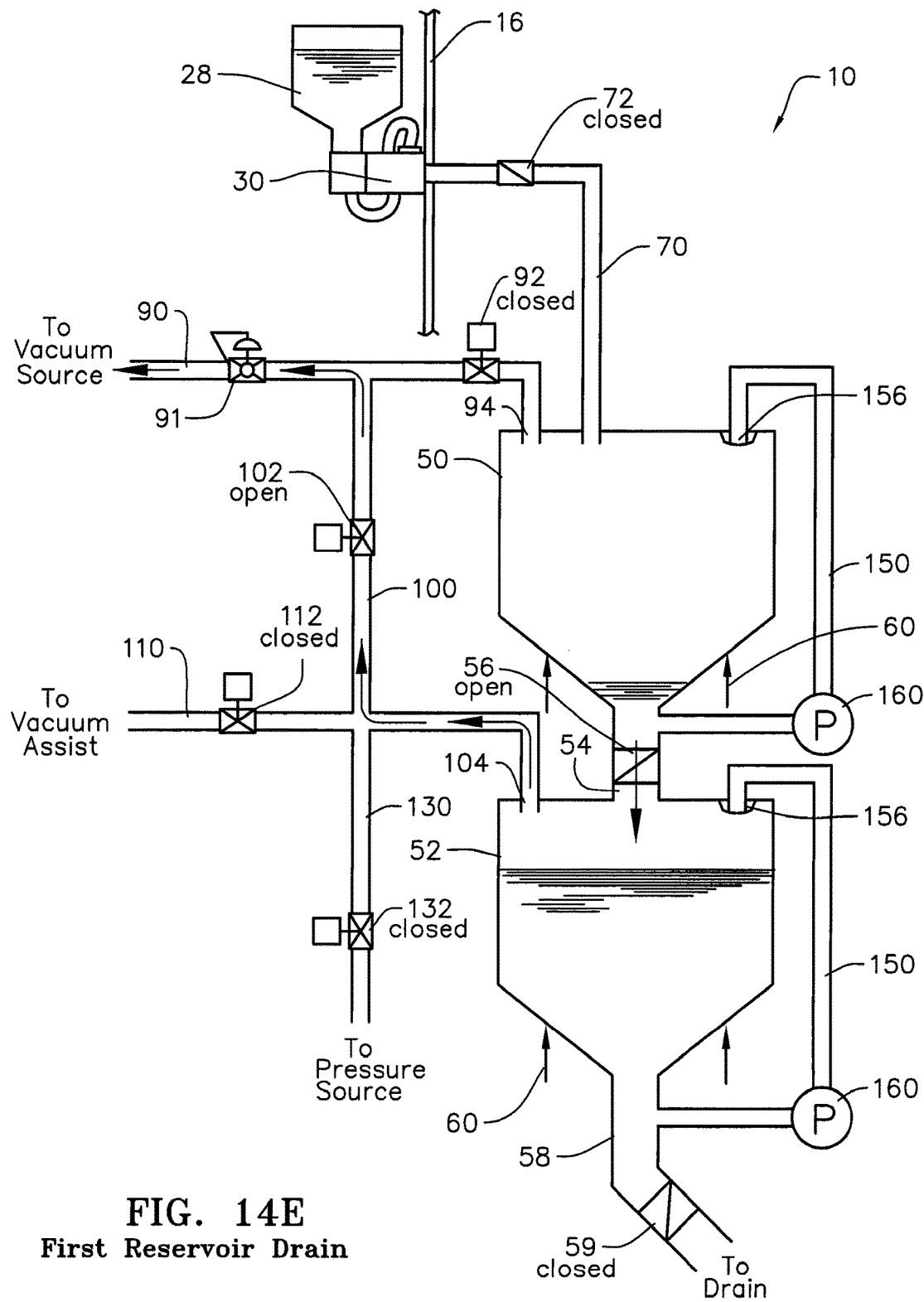
Figure 14F:
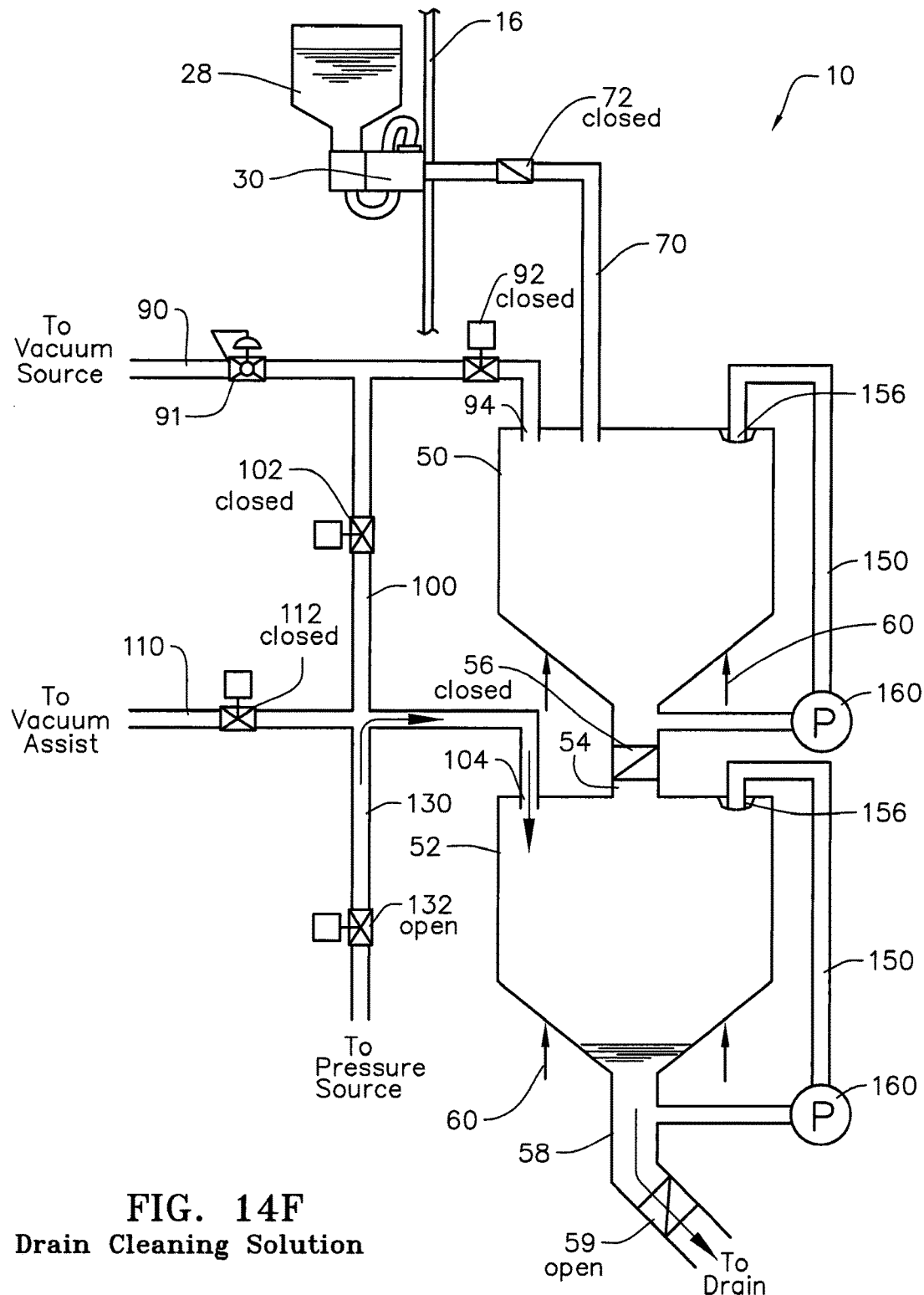

After a predetermined period of time of operating the recirculating pumps 160 to recirculate the initial volume of cleaning solution, the "First Reservoir Drain" phase as depicted in FIG. 14E is initiated by generating a signal to stop the recirculation pumps 160 and to open the auxiliary line valve 102 to bring the second reservoir to a negative pressure such that the bias of the fluid transfer check valve 56 is overcome and is forced to open, permitting the cleaning solution from the first reservoir 50 to flow or be drawn into the second reservoir 52.

Drain Cleaning Solution Phase—FIG. 9 Embodiment

When the cleaning solution in the first reservoir is drained (as detected by the load cells of the fluid sensor 60 on the first reservoir), the "Drain Cleaning Solution" phase as depicted in 14F is initiated by the PLC generating a signal to close the auxiliary line valve 102 and to open the pressure line valve 132. As air flows into the second reservoir, the bias of the check valve of the fluid discharge mechanism 59 is overcome, and the cleaning solution is evacuated from the second reservoir. Once the load cell of the fluid sensor on the second reservoir detects that the cleaning solution has been completely evacuated, the PLC generates a signal to repeat the "Cleaning Solution In", "Cleaning Solution Recirculation", and "Drain Cleaning Solution" phases until the cleaning solution bottle 28 is emptied and/or until the reservoirs are adequately cleaned.

The system 10 may incorporate a radio frequency identification (RFID) transceiver (not shown) which communicates with an RFID tagged cleaning solution bottle or bag 28 to ensure compliance with proper cleaning practices and warranty provisions. For example, the PLC of the system 10 may be programmed to prevent the "Suction Start" operation from being performed unless the system had previously performed a Clean Cycle using a recognized RFID tagged product. The PLC may also be programmed to recognize a unique RFID tag only once, so the same bottle or bag 28 cannot be refilled with a non-approved cleaner and then reused. Additionally the PLC may be programmed to accept only certain RFID tagged cleaning solution products produced within a certain date range to ensure that the cleaning solution has not exceeded its shelf-life.

In yet another alternative embodiment, the cleaning solution (or a separate sterilizing solution) may be disposed to be in fluid communication with the first reservoir 50 during the normal operation of the system instead of only during the cleaning cycle. The cleaning/sterilizing solution may be provided in bottles or bags or an internal or external refillable reservoir as previously described. The PLC may be programmed to periodically and/or continuously dispense the cleaning/sterilizing solution into the first reservoir 50, via gravity, negative pressure or via a pump, at the same time as the aspirated fluid enters the first reservoir 50 to immediately destroy any pathogens and or accelerate the breakdown of the biological material in the aspirated fluid before the fluid is discharged into the sanitary sewer.

The foregoing description is presented to enable one of ordinary skill in the art to make and use the invention and is provided in the context of a patent application and its requirements. Various modifications to the preferred embodiment of the apparatus, and the general principles and features of the system and methods described herein will be readily apparent to those of skill in the art. Thus, the invention is not to be limited to the embodiments of the apparatus, system and methods described above and illustrated in the drawing figures, but is to be accorded the widest scope consistent with the spirit and scope of the appended claims.

The invention claimed is:

1. A method of continuously collecting and disposing of fluid during a medical procedure without interruption and without limitation of the volume of the fluid capable of being collected during the medical procedure, the method comprising the steps of:
   (a) drawing fluid from a fluid source into a first reservoir in communication with a vacuum source, the communication with the vacuum source producing a substantially constant and continuous negative pressure in the first reservoir at all times during the medical procedure without interruption;
   (b) the fluid drawn into the first reservoir passing through an open fluid transfer valve into a second reservoir in communication with the vacuum source, the communication with the vacuum source producing a negative pressure in the second reservoir, wherein the fluid transfer valve is a check valve biased in a normally closed position;
   (c) the fluid transfer valve closing after a predetermined volume of the fluid passes into the second reservoir, while at all times during the medical procedure, additional fluid continues to be drawn into the first reservoir;
   (d) measuring the fluid in the second reservoir;
   (e) evacuating the fluid from the second reservoir through a discharge mechanism;
   (f) repeating steps (b) through (e) until the medical procedure is completed;
   whereby during all the steps (a)-(f), the first reservoir remains in uninterrupted communication with the vacuum source such that fluid from the fluid source is continuously drawn into the first reservoir without interruption and without limitation of the volume of the fluid collected during the medical procedure until the medical procedure is complete.

2. The method of claim 1 further including the step of relieving the negative pressure in the second reservoir prior to measuring the fluid in the second reservoir.

3. The method of claim 2 wherein the step of relieving the negative pressure in the second reservoir includes venting the second reservoir to atmosphere.

4. The method of claim 2 wherein the step of relieving the negative pressure in the second reservoir includes providing positive pressure to the second reservoir.

5. The method of claim 1 wherein the step of evacuating the fluid from the second reservoir includes pressurizing the second reservoir from a pressure source.

6. The method of claim 1 wherein the step of measuring the fluid collected in the second reservoir includes determining a level of the fluid in the second reservoir.

7. The method of claim 1 wherein the step of measuring the fluid collected in the second reservoir includes determining a volume of the fluid in the second reservoir.

8. The method of claim 1 wherein the step of measuring the fluid collected in the second reservoir includes determining a weight of the fluid in the second reservoir.

9. The method of claim 1 wherein the steps of measuring and evacuating the fluid are performed by a metering pump.

10. The method of claim 1 wherein the check valve is opened from the normally closed position by a negative pressure differential between the second reservoir and the first reservoir.

11. The method of claim 1 wherein the discharge mechanism is a drain valve.

12. The method of claim 11 wherein the drain valve is an electronically controllable valve.

13. The method of claim 12 wherein a controller generates a signal to open and close the drain valve.

14. The method of claim 11 wherein the drain valve is a check valve biased in a normally closed position.

15. The method of claim 14 wherein the check valve is opened from the normally closed position by a positive pressure in the second reservoir.

16. The method of claim 1 wherein the discharge mechanism is a pump.

17. The method of claim 1 further comprises a cleaning processes initiated after completion of the medical procedure, the cleaning process comprising:

(i) drawing cleaning solution from a cleaning solution source into the first reservoir in communication with the vacuum source, the communication with the vacuum source producing a negative pressure in the first reservoir;

(ii) the cleaning solution drawn into the first reservoir passing through the open fluid transfer valve into the second reservoir in communication with the vacuum source, the communication with the vacuum source producing a negative pressure in the second reservoir;

(iii) after a predetermine volume of the cleaning solution enters the second reservoir, preventing communication of the second reservoir with the vacuum source;

(iv) circulating the cleaning solution through the first and second reservoirs;

(v) draining the cleaning solution from the first and second reservoirs.

18. The method of claim 17, wherein steps (i)-(v) are repeated at least once.

19. The method of claim 17 wherein the cleaning solution source is a bottle of cleaning solution.

20. The method of claim 19 wherein step (i) is initiated by rotating the bottle from a first upright position to an inverted position.

* * * * *